United States Patent [19]

Marquez et al.

[11] Patent Number: 5,459,256

[45] Date of Patent: Oct. 17, 1995

[54] LIPOPHILIC, AMINOHYDROLASE-ACTIVATED PRODRUGS

[75] Inventors: Victor E. Marquez, Gaithersburg; John S. Driscoll, Rockville; Harry Ford, Jr., Bethesda; James A. Kelley, Silver Spring; Joseph J. Barchi, Jr., Bethesda; Hiroaki Mitsuya, Rockville; Christopher K-H. Tseng, Burtonsville; David G. Johns, Bethesda; Joseph E. Tomaszewski, Rockville, all of Md.

[73] Assignee: The Government of the United States of America as represented by the Department of Health and Human Services, Washington, D.C.

[21] Appl. No.: 683,432

[22] Filed: Apr. 10, 1991

Related U.S. Application Data

[63] Continuation-in-part of Ser. No. 313,056, Feb. 16, 1989, which is a continuation-in-part of Ser. No. 288,652, Dec. 12, 1988, abandoned, which is a continuation-in-part of Ser. No. 39,402, Apr. 17, 1987, abandoned.

[51] Int. Cl.$^6$ ................................................ C07H 19/16
[52] U.S. Cl. .................. 536/27.14; 536/27.6; 536/27.8; 536/27.81
[58] Field of Search ............... 536/24, 27, 27.21, 536/27.6–27.63, 27.7, 27.8, 27.81, 27.14, 27.61, 27.62

[56] References Cited

U.S. PATENT DOCUMENTS

| | | | |
|---|---|---|---|
| 2,928,773 | 3/1960 | Klein | 435/88 |
| 4,704,357 | 11/1987 | Mitsuya et al. | 514/45 |
| 4,711,955 | 12/1987 | Ward et al. | 514/45 |
| 4,751,221 | 6/1988 | Watanabe et al. | 514/45 |
| 4,788,181 | 11/1988 | Driscoll et al. | 514/49 |
| 4,880,782 | 11/1989 | Eckstein et al. | 514/45 |
| 4,882,316 | 11/1989 | Lambert et al. | 514/49 |
| 4,886,785 | 12/1989 | Lambert et al. | 514/50 |
| 4,908,440 | 3/1990 | Sterzycki et al. | 536/28.2 |
| 4,963,662 | 10/1990 | Matthes et al. | 514/45 |
| 5,106,837 | 4/1992 | Carson et al. | 514/45 |

OTHER PUBLICATIONS

Watanabe et al., J. Med. Chem., vol. 27, pp. 91–94 (1984).
Cheng et al., J. Biol. Chem., vol. 262, No. 5, pp. 2187–2189 (1987).
Lin et al., Biochem Pharmacol., vol. 36, No. 3, pp. 311–316 (1987).
Harada et al. J. Med. Chem., vol. 30, pp. 226–229 (1987).
Mikhailov et al., Bioorg. Khim., vol. 12, No. 5, pp. 626–632 (1986).
Herdewijn et al., J. Med. Chem., vol. 30, pp. 2131–2137, (1987).
Sandstrom et al., Drugs, vol. 34, pp. 372–390, 1987.
Mitsuya et al., Retroviruses in Human Lymphoma/Leukemia, Miwa et al. (EDS) Tokyo pp. 277–288 (1985).

*Primary Examiner*—Douglas W. Robinson
*Assistant Examiner*—James O. Wilson
*Attorney, Agent, or Firm*—Morgan & Finnegan

[57] ABSTRACT

The present invention relates, in general, to prodrugs. In particular, the present invention relates to lipophilic, aminohydrolase-activated, anti-viral nucleoside prodrug compounds, pharmaceutical compositions containing these compounds, and methods of using these compounds.

18 Claims, 5 Drawing Sheets

1 a) X=H;      Y=NH$_2$;      Z=H
b) X=H;      Y=OH;          Z=H
c) X=H;      Y=H;           Z=H
d) X=H;      Y=NH$_2$;      Z=CH$_3$
e) X=H;      Y=NHCH$_3$;    Z=CH$_3$
f) X=H;      Y=NHCH$_3$;    Z=H
g) X=H;      Y=NHCOPh;      Z=H
h) X=CH$_3$; Y=NH$_2$;      Z=H
i) X=H;      Y=Cl;          Z=H

1a, X=NH₂
1f, X=NHCH₃
1i, X=Cl

LIPOPHILIC, AMINOHYDROLASE-ACTIVATED PRODRUGS

BACKGROUND OF THE INVENTION

This application is a continuation-in-part of application Ser. No. 07/313,056 filed Feb. 16, 1989 which is a continuation-in-part of application Ser. No. 07/288,652 filed Dec. 12, 1988, now abandoned, which is a continuation-in-part of application Ser. No. 07/039,402 filed Apr. 17, 1987, abandoned, the contents of all of which are incorporated herein by reference.

1. Field of the Invention

The present invention relates, in general, to prodrugs. In particular, the present invention relates to lipophilic antiviral and anticancer nucleoside prodrugs activated by endogenous aminohydrolase enzymes.

2. Background Information

Nucleoside analogues are currently used as the primary mode of drug treatment for almost all viral diseases caused by human immunodeficiency virus (HIV) and the herpes virus family (herpes simplex I and II, varicella-zoster, cytomegalovirus, Epstein-Barr). This class of compounds is also useful for treating certain types of cancer. HIV causes AIDS, while the various members of the herpes family cause a range of problems (cancer, genital warts, shingles, herpes encephalitis). Many of these afflictions are fatal if not successfully treated. When the causative agent (virus or cancer cell) spreads to a sanctuary in the body (central nervous system (CNS), testes, eye, etc), drug treatment is often difficult because conventional active drugs have difficulty reaching the target organ site. Prodrugs designed to overcome these transport problems, especially to the CNS, and then be activated by endogenous aminohydrolases to active drugs, are described here.

Acquired immune deficiency syndrome, or AIDS, is a fatal disease which has reached epidemic proportions among certain high risk groups. Several features of AIDS make therapy extremely difficult. The main target of the AIDS virus, now known as HIV, or human immunodeficiency virus, is the T4 lymphocyte, a white blood cell that marshals the immune defenses. This depletion of T4 cells in AIDS causes a severe depression of the immune response, so that a compound which is to be effective against AIDS must modify virus effect without much help from host immunity. Furthermore, the virus also affects cells in the central nervous system (Berger, J. R. & Resnick, L. in AIDS. Modern Concepts and Therapeutic Challenges, Broder, S., Ed., M. Dekker, N. Y., 1987, pp 263–283; Snider, W. D. et al. *Ann Neurol.* 1983, 14, 403; Fauci, A. S. *Science* 1988, 239, 617; Price, R. W. et al; *Science* 1988, 239, 586; Lane, H. C. & Fauci, A. S. in AIDS. Modern Concepts and Therapeutic Challenges, Broder, S., Ed., M. Dekker, N.Y., 1987, pp 185–203), where it is protected by the blood-brain barrier from compounds that might otherwise be effective against the virus (Mitsuya, Ho & Broder, S. *Nature* 1987, 325, 773; De Clercq, E. *J. Med. Chem.* 1986, 29, 1561; Mitsuya, H. & Broder, S. *Proc. Nat. Acad. Sci. USA* 1986, 83, 1911). In infecting its host, the HIV binds to specific cell-surface receptor molecules. The virus penetrates the cell cytoplasm and sheds its protein coat, thereby baring its genetic material, a single strand of RNA. A viral enzyme, reverse transcriptase, accompanies the RNA. The virus, which is a retrovirus, reverse transcribes the RNA into DNA. Ultimately, some DNA copies of the HIV genome become integrated into the chromosomes of the host cell.

This integrated viral genome, known as a provirus, may remain latent until the host cell is stimulated, such as by another infection. The proviral DNA is then transcribed into mRNA, which directs the synthesis of viral proteins. The provirus also gives rise to other RNA copies that will serve as the genetic material of viral progeny. The proteins and the genomic RNA congregate at the cell membrane and assemble to form new HIV particles, which then break off from the cell. Two HIV genes, tat and trs/art, appear to control this burst of replication, which destroys the cell. These genes code for small proteins that boost the transcription of proviral DNA and the synthesis of viral proteins.

Several compounds have been shown to reduce the activity of reverse transcriptase in vitro. The reverse transcription is the step that is essential to viral replication and irrelevant to host cells. It has been found that HIV replication is considerably slower in the presence of compounds such as suramin, antimoniotungstate, phosphonoformate, and a class of nucleoside analogues known as dideoxynucleosides (ddN).

Nucleoside analogues are a class of synthetic compounds that resemble the naturally occurring nucleosides, which are chemical precursors of DNA and RNA. A nucleoside comprises a single-or double-ring base linked to a five-carbon sugar molecule. An analogue differs from the naturally-occurring nucleoside in large or small features of the base or the sugar. An enzyme that normally acts on a nucleoside in the course of viral replication may also bind to the nucleoside analogue. Because the nucleoside and the analogue differ, however, binding to the analogue can incapacitate the enzymes, thereby disrupting a molecular process crucial to viral replication.

Of the synthetic nucleoside analogues, dideoxyadenosine (ddA), dideoxyinosine (ddI) and dideoxycytidine (ddC), have been found to have potent in vitro activity against the human immunodeficiency virus (HIV) which causes AIDS. Additionally, dideoxycytidine has been found effective in vivo in treating patients with AIDS, and dideoxyinosine and dideoxyadenosine are currently being tested in vivo in patients with AIDS.

The blood-brain-barrier protects the brain from potentially harmful materials in the systemic circulation. Unfortunately, this phenomenon can also exclude useful drugs. (Greig, N. *Cancer Treat. Rev.* 1987, 14, 1) Lipophilic, non-ionic, low molecular weight materials generally appear to have the best passive diffusion properties for CNS penetration. (Rall, D. P. & Zubrod, C. G. *Annu. Rev. Pharmacol.* 1962, 2, 109) It also has been reported that an active transport mechanism may play a role in BBB penetration of some nucleosides (Collins, J. M. et al. *J. Pharmacol. Exp. Ther.* 1988, 245, 466; Conford, E. M. & Oldendorf, W. H. *Biochem. Biophys. Acta* 1975, 394, 211) although the structural requirements necessary to make use of this possibility are not well defined.

In an attempt to provide new antiviral and anticancer drugs by enhancing in vivo transport properties in general, and CNS transport properties in particular, the present invention specifically provides purine and pyrimidine nucleoside prodrugs. These compounds, because of their lipophilic, biologically stable character, can be transported after administration to disease-site sanctuaries and then converted by endogenous aminohydrolases to active anti-HIV, anti-herpes or anticancer drugs. It has been found that adenosine deaminase can convert certain 6-substituted purine dideoxynucleoside prodrugs into antiretroviral (eg. HIV) active inosine and guanosine compounds. This general concept is also valid for prodrugs of certain other nucleosides and their analogues, including acyclic, purine-containing nucleosides which are antivirally active. The conversion of certain 4-substituted pyrimidin-2-one nucleoside prodrugs by cytidine deaminase to antiretroviral, antiviral and anticancer compounds is also possible. The prodrugs proposed, because of their need to be activated by an aminohydrolase, are, by definition, prodrugs of active inosine, guanosine, uridine, and thymidine analogues.

SUMMARY OF THE INVENTION

It is an object of this invention to provide synthetic nucleosides which are prodrugs, subject to activation by aminohydrolases.

It is a specific object of this invention to provide synthetic nucleosides which have diffusion properties appropriate for CNS penetration.

It is another object of the invention to provide synthetic lipophilic nucleosides.

It is a further object of the invention to provide antiviral and anticancer pharmaceutical compositions.

It is another object of the invention to provide a method of treating a patient infected with a virus or cancer.

Further objects and advantages of the present invention will be clear from the description that follows.

DETAILED DESCRIPTION OF THE INVENTION

Figure 1:
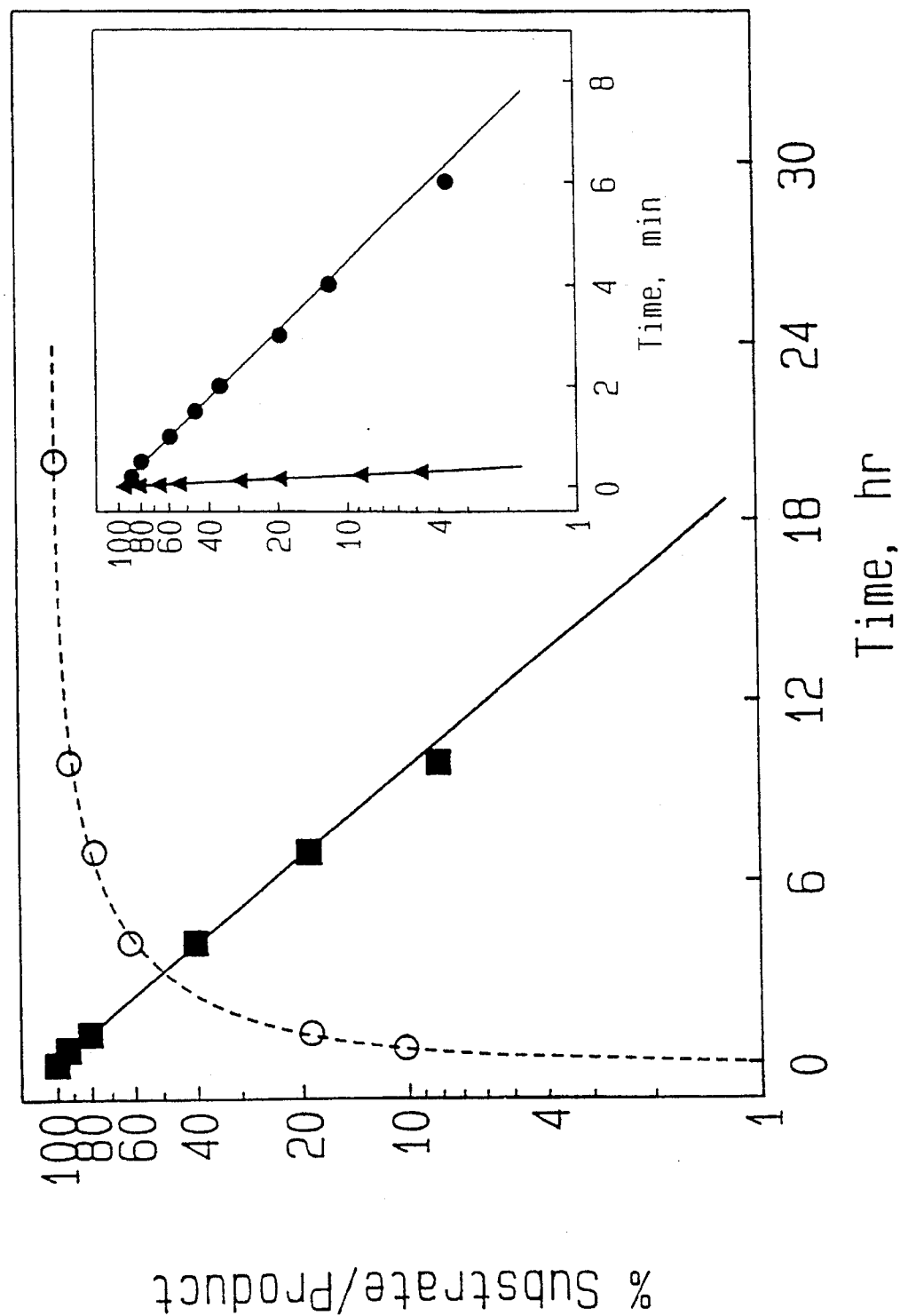
FIG. 1. Deamination of dideoxyadenosine analogues by adenosine deaminase. Hydrolysis kinetics and 2'-F-dd-ara-I formation during the incubation of 50 μM $N^6$-$CH_3$-2'-F-dd-ara-A (1f) with 0.7 units/mL of adenosine deaminase at 37° C. A unit of adenosine deaminase is the amount of enzyme which hydrolyzes a standard substrate (e.g., adenosine) at the rate of 1.0 μmole/min at 25° C. and pH 7.5. Symbols and measured $t_{1/2}$: $N^6$-$CH_3$-2'-F-dd-ara-A (■), 3.0 hr; 2'-F-dd-ara-I (o), 3.0 hr [appearance $t_{+c,fra\ 2+cc}$]. Insert: Adenosine deaminase hydrolysis kinetics for 50 μM ddA and 2'-F-dd-ara-A. The hydrolysis curve for ddA has been extrapolated from kinetics obtained with 0.07 units/mL of adenosine deaminase under identical conditions. Symbols and measured $t_{+c,fra\ 2+cc}$: ddA (▲), 5 sec; 2'-F-dd-ara-A (•), 1.33 min.

Nucleosides and their analogues are known for their antiviral properties against retroviruses (eg. dideoxynucleosides vs. HIV) and herpes viruses (eg. acyclovir, DHPG, and PMEA vs. the herpes simplex family). This class of compounds also has activity as anticancer drugs (eg. IUDR). The in vivo biochemical pharmacology of a prodrug is important relative to whether an analogue has properties which are superior to the active parent compound. Important properties are activity, potency, and in vivo transport to an organ site which the parent compound reaches only with difficulty.

Transport optimization is the property addressed through the design and synthesis of a selective set of 6-substituted purine-, and 4-substituted pyrimidine nucleoside analogues. The advantage of administering the proposed prodrugs, relative to their active parent compounds, is related to three factors. Prodrugs can be designed 1) to be more lipophilic than the parent compound which allows greater biological membrane penetration and therefore greater access to disease sanctuaries such as the CNS, 2) to have lower toxicity because the nucleoside prodrugs are poorer substrates for anabolic kinases. This allows the prodrug to be transported to its site of action (eg. CNS) in its inactive nucleoside form before aminohydrolase conversion and subsequent metabolic nucleotide formation, and 3) to allow the inactive prodrug to be converted to the active parent compound at its target site (eg. CNS) by endogenous enzymes (eg. aminohydrolases) which are abundant in the human body.

In vitro testing experiments with certain nucleoside analogues can give misleading results relative to a new compound's clinical potential. These analogues are 6-substituted purine and 4-substituted pyrimidine nucleosides. This is because some of these compounds have the ability to be converted by aminohydrolase enzymes to active agents. Examples of this are experiments detailed below which show that Compounds 1f and 1i, which have only moderate anti-HIV activity in the ATH8 cell culture tests, can have activity abolished when the potent adenosine deaminase inhibitor, 2'-deoxycoformycin (dCF) is added to the test system. Conversely, when extra adenosine deaminase (0.7 unit) was added to the test system, the activity of 1f was increased to 90% protection of ATH8 cells from the cytopathogenic effects of HIV. The manner in which the usual test procedure can be misleading relative to a new compound's clinical potential is related to the fact that the level of the aminohydrolase enzymes (eg. adenosine deaminase) in the cell culture test systems is very low relative to the levels in the human body. Therefore, compounds capable of being enzymatically hydrolyzed to an active drug, but which are converted slowly in vitro due to the low enzyme level, will appear to be poor candidate drugs. These same compounds, even though poor substrates for the aminohydrolases, would be hydrolyzed at an appropriate rate in patients to an active drug because of the large amount of enzyme present in mammals. The rate of hydrolysis would be determined by the prodrug structure which can be fine-tuned to allow for prodrug transport to the intended site (eg. CNS) and the controlled sustained or slow release of active material in the target organ by action of the endogenous aminohydrolase.

Hansch and co-workers have pioneered the use of octanol-water partition coefficients (log P) to correlate compound structure with CNS penetration. (Hansch, C. et al. D. J. Med. Chem. 1967, 11, 1) This was the applicants starting point for maximizing the CNS anti-AIDS activity for the 2', 3'-dideoxynucleoside series (Driscoll, J. et al. Vth Internat. Conf. on AIDS, Montreal, 1989, M.C.P. 107).

The log P of AZT indicates that this compound is really neither lipophilic nor hydrophilic but partitions into octanol and pH 7.0 buffer almost equally. AZT, however, is one of the more lipophilic compounds investigated clinically, and it enters the CNS better than ddC (Collins, J. M. et al. J.

*Pharmacol. Exp. Ther.* 1988, 245, 466; Broder, S. *Medical Res. Rev.* 1990, 10, 419). The failure of ddC to achieve significant CNS levels might be related to the more hydrophilic nature of this compound relative to AZT. Thus, ddN more lipophilic than AZT for anti-HIV evaluation were prepared.

An uncertain aspect of designing lipophilic compounds is retention of anti-HIV activity after making the appropriate structural modifications, since the activity of dideoxynucleosides is critically dependent on a series of enzymatic events, any one of which might be adversely affected by a structural change. For this reason, the most minor structural changes possible—the addition of a methyl group (which should increase a log P value by ca. 0.5) (Leo, A. et al. Chem. Rev. 1971, 71, 525) at various purine positions were made. Purines rather than pyrimidines were modified initially, because purines are the more lipophilic class. Among the dideoxypurines, ddA was chosen to modify rather than ddI for the same reason, and a 2'-fluoro substituent was normally included for its acid stabilizing properties. (Marquez, V. E. et al. *J. Med. Chem.* 1990, 33, 978)

In the following embodiments, monophosphate, diphosphate, and triphosphate are defined as:

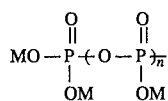

if n=0 then monophosphate,
if n=1 then diphosphate, and
if n=2 then triphosphate;
wherein when the counter ion (M) is necessary the counter ion is an alkyl metal (more specifically, $Na^+$ or $K^+$), $NH_4^+$, or H.

In one embodiment, the present invention relates to a compound of formula (I)

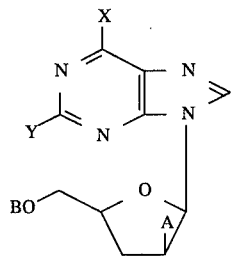

wherein A is H or F;,
B is H, monophosphate, diphosphate, or triphosphate wherein when the counter ion is necessary the counter ion is an alkyl metal (preferably, $Na^+$ or $K^+$), H, or $NH_4^+$;
Y is H, $NH_2$, or halogen (F, Cl, Br, I);
X is NHR, $NR_2$, NROR, halogen, SR, or OR' wherein R is H, $C_1$–$C_{16}$ alkyl (branched or unbranched), or $(CH_2)_{1-8}Ar$; and R' is $C_1$–$C_{16}$ alkyl or $(CH_2)_{1-8}Ar$ wherein Ar is unsubstituted phenyl, or phenyl substituted with $C_1$–$C_8$ alkyl (preferably, unbranched) or OH; with the proviso that when A is H, X is not a halogen.

Preferrably, A is F, B is H, Y is H or $NH_2$, and X is a halogen (specifically, Cl) or $NH(C_1$–$C_8$ alkyl) (specifically, $NHCH_3$).

In another embodiment, the present invention relates to a compound of formula (II)

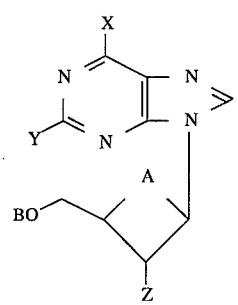

wherein A is O or $CH_2$;
B is H, monophosphate, diphosphate, or triphosphate wherein when the counter ion is necessary the counter ion is an alkyl metal (preferably, $Na^+$ or $K^+$), H, or $NH_4^+$;
Z is H, OH, or $CH_2OH$;
Y is H, $NH_2$, or halogen;
X is NHR, $NR_2$, NROR, halogen, SR, or OR' wherein R is H, $C_1$–$C_{16}$ alkyl (branched or unbranched), or $(CH_2)_{1-8}Ar$; and R' is $C_1$–$C_{16}$ alkyl (preferably, unbranched) or $(CH_2)_{1-8}Ar$ wherein Ar is unsubstituted phenyl, phenyl substituted with $C_1$–$C_8$ alkyl, or phenyl substituted with OH; with the proviso that when B is H, X may not be $NH_2$ or OH.

Preferably, B is H, Z is $CH_2OH$, Y is $NH_2$, and X is halogen (specifically, Cl) or $NH(C_1$–$C_8$ alkyl) (specifically, $NHCH_3$).

In a further embodiment, the present invention relates to a compound of formula (III)

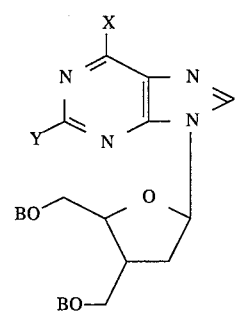

wherein B is H, monophosphate, diphosphate, or triphosphate wherein when the counter ion is necessary the counter ion is an alkyl metal (preferably, $Na^+$ or $K^+$), H, or $NH_4^+$;
Y is H, $NH_2$, or halogen;
X is NHR, $NR_2$, NROR, halogen, SR, or OR' wherein R is H, $C_1$–$C_{16}$ alkyl, or $(CH_2)_{1-8}Ar$; and R' is $C_1$–$C_{16}$ alkyl or $(CH_2)_{1-8}Ar$ wherein Ar is unsubstituted phenyl, phenyl substituted with $C_1$–$C_8$ alkyl, or phenyl substituted with OH.

Preferably, B is H, Y is H, and X is halogen (specifically, Cl) or $NH(C_1$–$C_8$ alkyl) (specifically, $NHCH_3$).

In yet another embodiment, the invention relates to a compound of formula (IV)

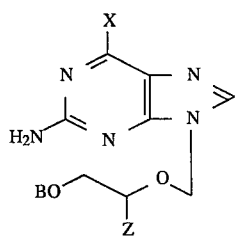

wherein B is H, monophosphate, diphosphate, or triphosphate wherein when the counter ion is necessary the counter ion is an alkyl metal (preferably, Na$^+$ or K$^+$), H, or NH$_4^+$;

Z is H, OH, or CH$_2$OH;

X is NHR, NR$_2$, NROR, halogen, SR, or OR' wherein R is H, C$_1$–C$_{16}$ alkyl, or (CH$_2$)$_{1-8}$Ar; and R' is C$_1$–C$_{16}$ alkyl or (CH$_2$)$_{1-8}$Ar wherein Ar is unsubstituted phenyl, phenyl substituted with C$_1$–C$_8$ alkyl, and phenyl substituted with OH.

Preferably, B is H, X is halogen or NH(C$_1$–C$_8$ alkyl) (specifically, X is Cl or NHCH$_3$), and Z is H or CH$_2$OH.

In a further embodiment, the present invention relates to a compound of formula (V)

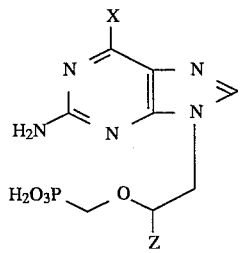

wherein Z is H, OH, or CH$_2$OH; and

X is NHR, NR$_2$, NROR, halogen, SR, or OR' wherein R is H, C$_1$–C$_{16}$ alkyl, or (CH$_2$)$_{1-8}$Ar; and R' is C$_1$–C$_{16}$ alkyl or (CH$_2$)$_{1-8}$Ar wherein Ar is unsubstituted phenyl, phenyl substituted with C$_1$–C$_8$ alkyl, and phenyl substituted with OH.

Preferably, X is halogen or NH(C$_1$–C$_8$ alkyl) (specifically, X is Cl or NHCH$_3$) and Z is H or CH$_2$OH.

In another embodiment, the present invention relates to a compound of formula (VI)

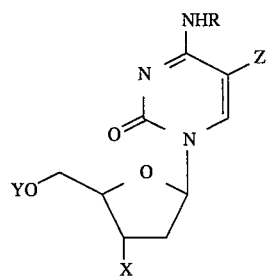

wherein X is H, F, or N$_3$;

Y is H, monophosphate, diphosphate, or triphosphate wherein when the counter ion is necessary the counter ion is an alkyl metal (preferably, Na$^+$or K$^+$), H, or NH$_4^+$;

Z is H, (CH$_2$)$_{0-5}$CH$_3$, or halogen; and

R is H, OH, O(CH$_2$)$_{0-5}$CH$_3$, C$_1$–C$_{16}$ alkyl, or (CH$_2$)$_{1-5}$Ar; wherein Ar is unsubstituted phenyl, phenyl substituted with C$_1$–C$_8$ alkyl, and phenyl substituted with OH.

Preferably, X is N$_3$, Y is H, R is C$_1$–C$_8$ alkyl (specifically, CH$_3$), and Z is C$_1$–C$_8$ alkyl (specifically, CH$_3$).

In a further embodiment, the present invention relates to a compound of formula (VII)

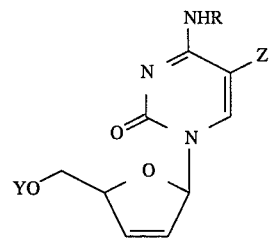

wherein Y is H, monophosphate, diphosphate, or triphosphate wherein when the counter ion is necessary the counter ion is an alkyl metal (preferably, Na$^+$ or K$^+$), H, or NH$_4^+$;

Z is H, (CH$_2$)$_{0-5}$CH$_3$, or halogen; and

R is H, OH, O(CH$_2$)$_{0-5}$CH$_3$, C$_1$–C$_{16}$ alkyl, or (CH$_2$)$_{1-5}$Ar; wherein Ar is unsubstituted phenyl, phenyl substituted with C$_1$–C$_8$ alkyl, and phenyl substituted with OH.

Preferably, Y is H, R is C$_1$–C$_8$ alkyl (specifically, CH$_3$), and Z is C$_1$–C$_8$ alkyl (specifically, CH$_3$).

In another embodiment, the present invention relates to a compound of formula (VIII)

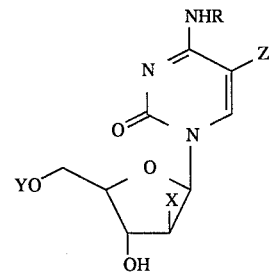

wherein X is H or F;

Y is H, monophosphate, diphosphate, or triphosphate wherein when the counter ion is necessary the counter ion is an alkyl metal (preferably, Na$^+$ or K$^+$), H, or NH$_4^+$;

Z is halogen or CH=CHBr; and

R is H, OH, O(CH$_2$)$_{0-5}$CH$_3$, C$_1$–C$_{16}$ alkyl, or (CH$_2$)$_{1-5}$Ar; wherein Ar is unsubstituted phenyl, phenyl substituted with C$_1$–C$_8$ alkyl, and phenyl substituted with OH.

Preferably, Y is H, Z is halogen (specifically, I), and R is C$_1$–C$_8$ alkyl (specifically, CH$_3$).

In yet another embodiment, the present invention relates to antiviral pharmaceutical compositions comprising the above-described compounds in an antivirally effective amount and a pharmaceutically acceptable diluent, carrier, or excipient.

Because the 2'-fluoro compounds of the present invention are stable in an acid environment such as is found in the human stomach, they can readily be formulated without the need for pH buffers into dosages suitable for oral administration, using a pharmaceutically acceptable carrier, diluent, or excipient, which are well known in the art. Such carriers may enable the compounds to be formulated as tablets, pills, capsules, liquids, gels, and the like, for oral ingestion by a patient to be treated for AIDS.

The precise dosage amounts to be administered will be determined by routine experimentation. In general, however, the dosage amounts will be comparable to those already known from the experimental use of dideoxy adenosine, AZT, acyclovir, DHPG, oxetanocin, HPMPA, PMEA, and IUDR.

Pharmaceutical compositions within the scope of the present invention include compositions wherein the active ingredient is contained in an effective amount to achieve its intended purpose. Determination of the effective amounts is well within the skill of the art.

In addition to the nucleosides of the present invention, these pharmaceutical compositions may contain suitable pharmaceutically acceptable carriers comprising excipients and auxiliaries which facilitate processing of the active compounds into preparations which can be used pharmaceutically. The preparations may be formulated for oral administration, and are in the form of tablets, dragees, and capsules. Alternatively, the preparations may be administered rectally, such as in the form of suppositories. Alternatively, solutions may be prepared for oral or parenteral administration. The compositions of the present invention contain from about 0.1 to 99 percent, and preferably from about 25 to 85 percent by weight of active ingredient, together with the excipient.

The pharmaceutical compositions of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture, and processing the mixture of granules, after adding suitable auxiliaries, if desired, to obtain tablets or dragee cores.

Suitable excipients are, in particular, fillers such as sugars, such as lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone. If desired, disintegrating agents may be added, such as the cross-linked polyvinyl pyrrolidone, agar, or alginic acid or a salt thereof such as sodium alginate. Auxiliaries which can be used include flow-regulating agents and lubricants, such as silica, talc, stearic acid or salts thereof such as magnesium or calcium stearate, and/or polyethylene glycol. Dragee cores are provided with suitable coatings. For this purpose, concentrated sugar solutions may be used, which may optionally contain gum arabic, talc, polyvinyl pyrrolidone, polyethylene glycol, and/or titanium dioxide, lacquer solutions, and suitable organic solvents or solvent mixtures. Dyestuffs or pigments may be added to the tablets or dragee coatings for identification or in order to characterize different combinations of active compound doses.

Other pharmaceutical preparations which can be used orally include push-fit capsules made of gelatin, as well as soft, sealed capsules made of gelatin and a plasticizer, such as glycerol or sorbitol. The push-fit capsules can contain the active ingredients in a mixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Although many of the anti-HIV compounds of the invention are designed to be administered orally because of their stability in low pH environments such as in gastric juices, pharmaceutical preparations may be prepared for parenteral administration, especially for antiviral and anticancer prodrugs. Suitable formulation for parenteral administration include aqueous solutions of the prodrugs in water-soluble form. Additionally, suspensions of the compounds may be prepared as appropriate oily injection suspensions. Suitable lipophilic solvents or vehicles include fatty oils such as sesame oil, or synthetic fatty acid esters, such as ethyl oleate or triglycerides. Aqueous injection suspensions may contain substances which increase the viscosity of the suspension, such as sodium carboxymethyl cellulose, sorbitol, and/or dextran. Optionally, the suspension may also contain stabilizers.

In a further embodiment, the present invention relates to a method of treating a patient infected with a virus comprising administering to the patient an amount of the above-described compounds sufficient to effect said treatment. Preferably, the therapeutically effective amount is sufficient to inhibit viral replication in cells infected with a retrovirus or is sufficient to inhibit the infectivity of a retrovirus.

Once the prodrugs are converted by endogenous aminohydrolase enzymes to active compounds, the mechanism of action is as previously established (inhibition of retrovirus reverse transcriptase, inhibition of viral DNA polymerase after herpes-induced thymidine kinase activation or incorporation into cancer cell DNA).

The present invention is described in further detail in the following non-limiting examples.

EXAMPLES

The following protocols and experimental details are referenced in the examples that follow:

Melting points were taken on a Mel-Temp II apparatus and were uncorrected. UV spectra were recorded on a Beckman model 34 spectrophotometer or on-the-fly during HPLC analysis on a Perkin-Elmer LC-235 array spectrophotometer. Optical rotations were recorded on a Perkin-Elmer 241 polarimeter at the sodium D line. Infrared spectra were recorded on a Perkin-Elmer 727B spectrophotometer. Proton and $^{13}$C NMR spectra were run on a Variant XL-200 spectrometer at 200 and 50 MHz, respectively. Chemical shifts are given in ppm relative to TMS and are referenced against the solvent in which the samples were run. Analytical and preparative TLC analyses were performed on Uniplate GHLF silica gel (Analtech, 250 and 1000 microns, respectively). Column chromatography was accomplished with Kieselgel 60 (mesh size 230–400). Reverse phase purification was performed either on $C_{18}$ disposable extractions columns (J. T. Baker, 6 ml) or at medium pressure on bonded phase $C_{18}$ silica gel. Moisture sensitive reactions were run under argon in flasks previously dried at 110° C. Ether and THF were distilled from sodium/benzophenone ketyl. All other solvents came from Sure Seal bottles purchased from Aldrich. Silylation reagents were premixed in 1 ml vials and purchased from Alltech.

Figure 2:
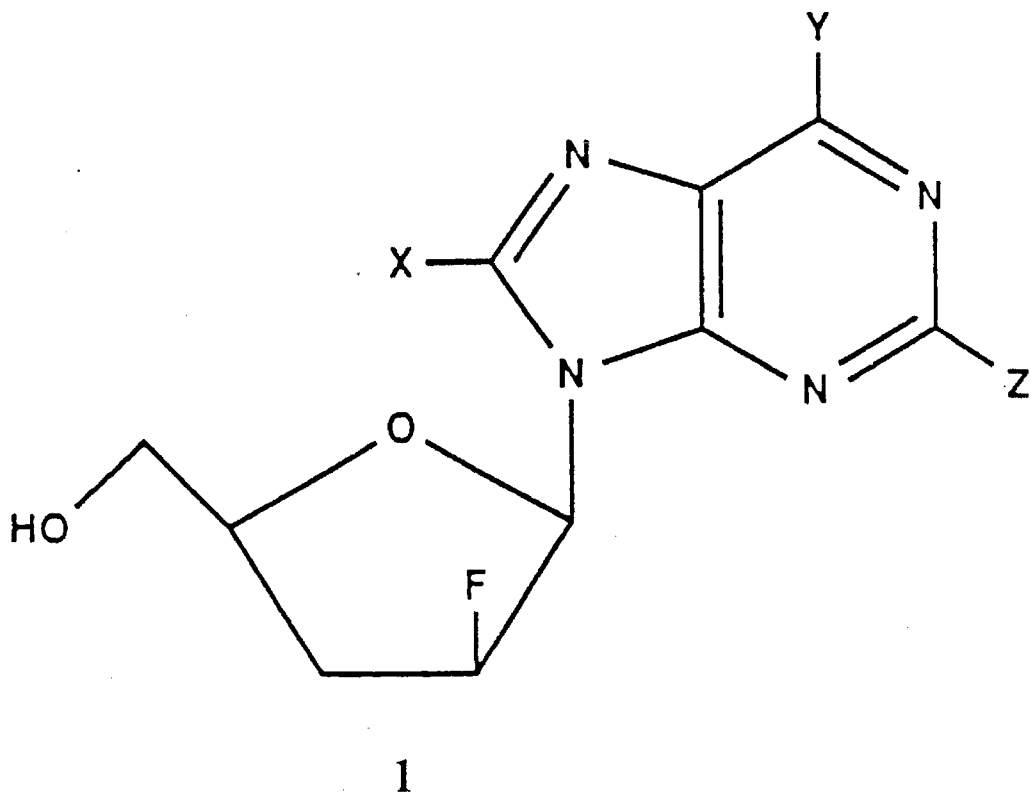
FIG. 2. Generalized structural formula for dideoxypurine nucleosides.
Figure 3:
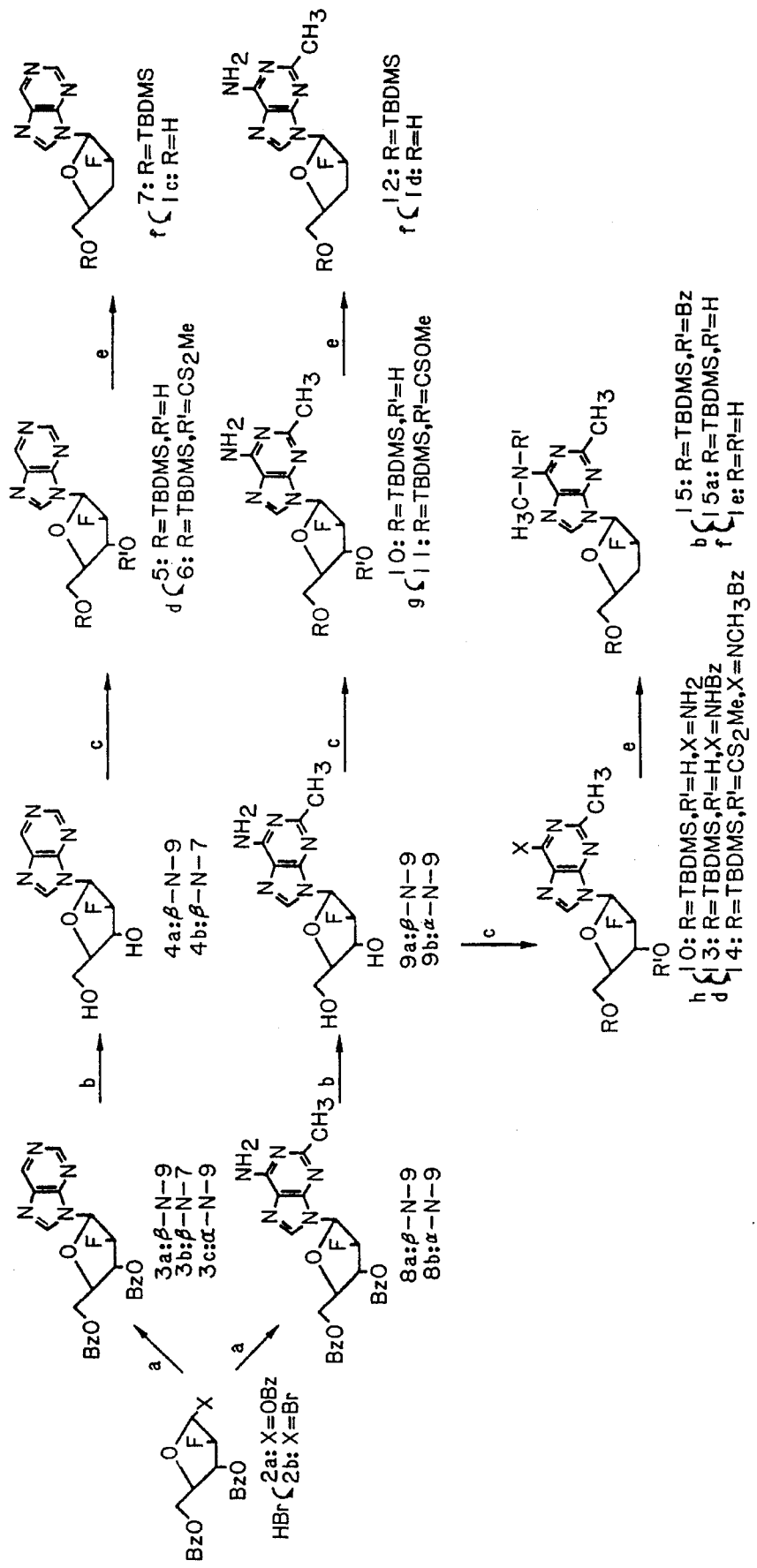
FIG. 3. Synthetic scheme 1. (a) TMS-base, neat, 100° C.; (b) $NH_3$/MeOH; (c) TBDMS-Cl, imidazole, DMF; (d) $CS_2$, NaH, MeI, DMF; (e) $Bu_3SnH$, AIBN, Toluene, 90° C.; (f) 80% AcOH, 90° C.; (g) 1,1'-thiocarbonyldiimidazole, DMF then MeOH, reflux; (h) BzCl, Pyr, then NaOH.
Figure 4:
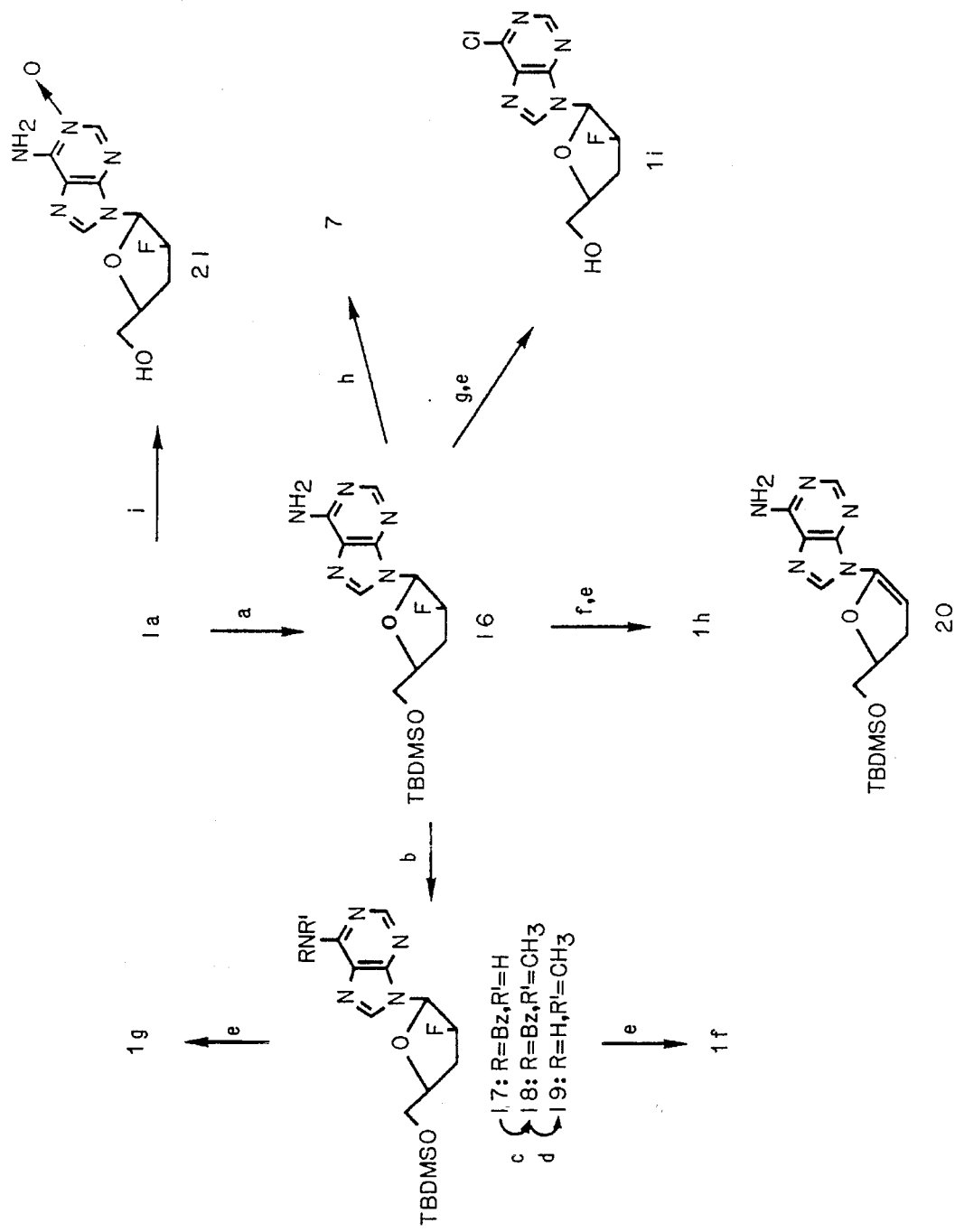
FIG. 4. Synthetic scheme 2. (a) TBDMS-Cl, imidazole, DMF; (b) BzCl, Pyr, then NaOH; (c) NaH, MeI, DMF; (d) $NH_3$/MeOH; (e) 80% AcOH; (f) LDA, MeI, −78° C.; (g) t-BuONO, $CCl_4$, 85° C., 200 watt bulb; (h) t-BuONO, THF, 85° C., 200 watt bulb; (i) $H_2O_2$, AcOH.
Figure 5:
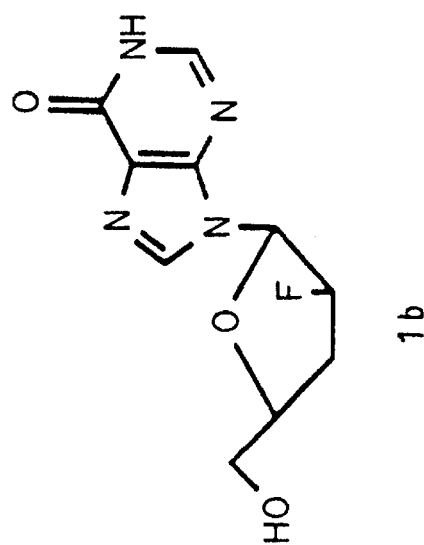
FIG. 5. Scheme 3, deamination of 2'-fluoro-substituted-2', 3'-dideoxyadenosine analogs by adenosine deaminase.
Figure 5:
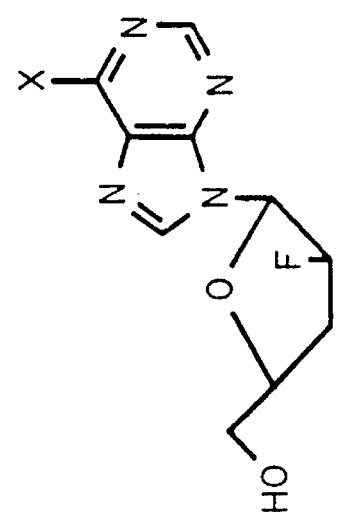

Positive ion fast atom bombardment mass spectra were obtained on a VG 7070E mass spectrometer operated at an accelerating voltage of 6 kV and a resolution of 2000. Glycerol was used as the sample matrix and ionization was effected by a beam of xenon atoms derived by charge-exchange neutralization of a 1.0–1.2 mA beam of xenon ions accelerated through 8.0–9.2 kV. Spectra were acquired under the control of a VG 11/250 J$^+$ data system at a scan speed of 10 s/decade, and the background due to the glycerol matrix was automatically subtracted. Accurate mass measurements of the protonated molecular ions (MH$^+$) for compounds 1d and 1i (FIG. 2) were obtained by a limited mass range voltage scan at a resolution of 3000 with repetitive data accumulation and averaging under computer control. The MH$^+$ peak was then mass measured with the appropriate data system software using selected glycerol peaks within the mass range as internal references.

A 50 μl aliquot of a 10 mg/ml suspension of adenosine deaminase (adenosine aminohydrolase, EC 3.5.4.4) from calf intestinal mucosa was centrifuged at 600×g for 3 min. The residue remaining after removal of the $(NH_4)_2SO_4$ supernatant was dissolved in 0.5 ml pH 7.4 tris(hydroxymethyl)-aminomethane (Tris) buffer to give an enzyme solution of 1 mg/ml (274 units/ml). 2'-Deoxycoformycin (dCF), 2', 3'-dideoxy-2'-fluoroarabinosyladenine (2'-F-dd-ara-A, 1a) and 2', 3'-dideoxy-2'-fluoroarabinosylhypoxanthine (2'-F-dd-ara-I, 1b) were obtained from the Pharmaceutical Resources Branch, NCI. A pH 7.4 buffer was prepared by adjusting 0.01M Tris to pH 7.4 with 0.5N HCl, The 1.0 HCl , HPLC-grade acetonitrile, monobasic potassium phosphate, sodium hydroxide and ultrapure Tris were all commercially available and were used without further purification.

Enzymatic Deamination of Adenosine Analogues. Solutions (1 mM) of dideoxynucleoside substrates (ddA, 1a, 1f, 1g, 1i and 21) (FIG. 2) were prepared in 0.01M pH 7.4 Tris buffer, while 1 mM and 2 μM solutions of the adenosine deaminase inhibitor, 2'-deoxycoformycin, were prepared in distilled water. A 50 μL aliquot of substrate solution was diluted with 0.95 ml 0.01M Tris buffer in a 1.5-mL Eppendorf tube and equilibrated at 37° C. in a Dubnoff metabolic shaking incubator. Reaction was initiated by addition of 2.5 μL of adenosine deaminase solution (0.7 unit). At specified time intervals, a 50 μL aliquot of the reaction mixture was withdrawn and quenched by mixing with 0.45 mL cold 2 μM 2'-deoxycoformycin. This diluted sample was ultrafiltered to remove enzyme in a Centrifree Micropartition unit by centrifugation at 600×g at 4° C. in a high speed refrigerated centrifuge. The decrease in substrate concentration was monitored by HPLC analysis of the resultant ultrafiltrate (see below). The ability of 2'-deoxycoformycin to inhibit deamination under the above conditions was evaluated by adding 2 μL of 1.0 mM inhibitor to diluted substrate solutions at the time of equilibration. Reaction, sampling and analysis were carried out as above. In additional experiments, 4-6 concentrations of each substrate (ddA, 1a, 1f, 1i) were reacted with ADA (0.01, 0.03 or 0.4 units depending on substrate) at pH 7.4 and 37° C. Initial hydrolysis rates for each substrate concentration were measured through linear least-squares curve fitting of the concentration versus time data for reaction of the first 10% of substrate. $K_M$ and $v_{max}$ values for each substrate were then determined from a graphical lineweaver-Burke plot of these initial rates (FIG. 1).

HPLC Analysis of Dideoxypurine Nucleosides.

Concentrations of dideoxynucleosides were measured by the HPLC analysis of 100 μL aliquots of ultrafiltered samples. A 4.6×250 mm 5-μm Ultrasphere-ODS column, protected by a Waters guard column packed with 37–50 μm Vydac 201SC, was eluted with 10–20% $CH_3CN$ in 0.01M pH 7.0 phosphate buffer at a flow rate of 1.0 mL/min. Dideoxynucleosides and deamination products were detected at the appropriate wavelength of maximum absorption with a Gilson 116 variable wavelength detector. Peak identity was determined from coincidence of retention times with standards and by comparison of on-the-fly UV spectra obtained with a Perkin-Elmer LC-235 diode array detector. Peak areas and peak heights were measured simultaneously on a Spectra-Physics SP4200 computing integrator. For kinetic studies, this data was plotted as a function of time and, where possible, fitted to a first order decomposition using Graph-Pad, a commercial non-linear least squares, curve fitting program.

Measurement of Octanol-Water Partition Coefficients.

n-Octanol-water partition coefficients (P) were determined by a microscale shake-flask procedure, (Ford, H. et al *Abstracts of Papers,* 200th National Meeting of the American Chemical Society, Washington, D.C.; American Chemical Society: Washington, D.C., 1990; CARB 13) which was modification of an earlier method (Nahum, A. & Horvath, C. *J. Chromatogr.* 1980, 192, 315). A 20 μL aliquot of a 0.5 mg/mL DMSO solution of the dideoxynucleoside was dissolved in 1.0 mL of octanol-saturated, pH 7.0, 0.01M potassium phosphate buffer. This was mixed thoroughly with 1.0 ml of buffer-saturated n-octanol in a 2-mL Mixxor apparatus at 24°–26° C. and then allowed to stand for 15 min. The phases were separated, centrifuged at 600×g for 5 min, and the relative concentration of sample in each phase determined by HPLC analysis of a 50 μl aliquot. The partition coefficient was calculated by dividing the absolute area of the appropriate integrated peak from the octanol phase by that of the buffer phase (Table I).

HIV Cytopathic Effect Inhibition Assay.

The HIV cytopathic effect inhibition assay was performed as previously described. (Mitsuya, H. & Broder, S. *Proc. Nat. Acad. Sci. USA* 1986, 83, 1911) Briefly, 200,000 target CD4$^+$ ATH8 cells were exposed to cell-free HIV-1/III$_B$ at a dose of 43 (or 1087 for compound 1g) TCID$_{50}$ (50% tissue culture infectious dose) for 1 h, resuspended in 2 ml of fresh culture media containing interleukin 2, and cultured at 37° C. with or without test compounds in 5% $CO_2$-containing humidified air. On day 8 in culture, the viable cells were counted by using the dye exclusion method. All compounds, including inactives, were evaluated a minimum of two times in separate experiments. Data reported in Table II are from representative tests. The % protection against the virus was determined by the following formula: 100 times [(the number of viable cells exposed to HIV-1 and cultured in the presence of the compound minus the number of viable cells exposed to HIV-1 and cultured in the absence of compound) divided by (the number of viable cells cultured alone minus the number of viable cells exposed to HIV-1 and cultured in the absence of the compound)]. The % toxicity of a compound on the target cells was determined by the following formula: 100 times [1 minus (the number of total viable cells cultured in the presence of the compound divided by the number of total viable cells cultured alone)]. Calculated percentages equal to or less than zero are expressed as 0%.

See FIGS. 2–5 for synthetic schemes.

See Table V for the elemental analyses of new compounds.

EXAMPLE 1

Chemistry 9-(3', 5'-di-O-benzoyl-2'-deoxy-2'-fluoro-β-D-arabinofuranosyl)-9-H-purine (3a).

Purine (250 mg, 2.08 mmol) was suspended in dry acetonitrile (7 ml, argon atmosphere) and treated with BSTFA (1 ml vial, Pierce) at room temperature. After 30 min the homogeneous solution was evaporated to dryness in vacuo. The resulting yellow oil was placed under an argon atmosphere and compound 2b (807 mg, 1.90 mmol), dissolved in dry $CH_2Cl_2$ (10 ml), was added to the trimethylsilyl purine via syringe. After removing the solvent on the rotoevaporator (40° C.) the neat mixture was heated to 100° C. and rotated under vacuum for 45 min. After cooling to room temperature the resulting syrup was dissolved in $CH_2Cl_2$, filtered and concentrated. Purification on silica gel (1% MeOH/$CH_2Cl_2$-3% MeOH/$CH_2Cl_2$) afforded 564.2 mg (63.9%) of a 3:1 mixture of isomers 3a and 3b as a foam along with a minor amount (<5%) of 3c. $^1H$ NMR of the major component 3a ($CDCl_3$): δ9.19 (s, H2 or H6); 9.01 (s, H2 or H6); 8.40 (d, J=2.8 Hz, H8); 8.0–8.2 (m, aromatic); 7.3–7.7 (m, aromatic); 6.75 (dd, J=2.7 and 12.4 Hz, H1'); 5.80 (dd, J=2.7 Hz and 16.3 Hz, H3'); 5.38 (dd, J=2.7 and 49.8 Hz, H2'); 4.82 (d, H5', H5"); 4.62 (q, H4'). The mixture was carried through the next step.

9-(2'-deoxy-2'-fluoro-β-D-arabinofuranosyl)-9-H-purine (4a).

A 3:1 mixture of 3a and 3b (563 mg, 1.21 mmol) was placed in a pressure bottle and treated with a solution of ammonia saturated methanol (10 ml). The mixture was kept at 10 ° C. for 14 h. Argon was bubbled through the solution for 5 min and the methanol was removed. The resulting gum was taken up in water and washed with $CH_2Cl_2$ (3×). The aqueous layer was freeze dried and purified first by silica gel flash chromatography (FC) (5% MeOH/$CH_2Cl_2$ eluant) and subsequently by reverse phase chromatography ($C_{18}$, linear gradient of $H_2O$-10% MeOH/$H_2O$) affording 285 mg of the diol as a powder (92%) in the same isomer ratio (3:1). $^1H$ NMR (DMSO-$d_6$) for the major component 4a: δ9.22 (s, H2 or H6); 8.98 (s, H2 or H6); 8.75 (d, J=1.8 Hz, H8); 6.58 (dd, J=4.9 and 13.0 Hz,H1'); 5.30 (dt, J=4.4 Hz and 52.6 Hz, H2'); 4.49 (dt, J=4.4 and 19.0 Hz, H3'); 3.89 (q, J=4 9 Hz,H4'); 3.68 (m, H5', H5") This was also carried through to the next step. Anal. ($C_{10}H_{11}N_4O_3F$. 0.2 $H_2O$ ) C, H, N, F.

9-(5'-O-tert-butyldimethylsilyl-2'-deoxy-2'-fluoro-β-D-arabinofuranosyl)- 9-H-purine (5).

A mixture of 4a and 4b (285 mg, 1.12 mmol) was dissolved in dry dimethylformamide (DMF, 4 ml), treated with 2 ml of a premixed solution of TBDMS-Cl/imidazole in DMF (Alltech) at room temperature and stirred for 15 min. Water was added and the aqueous mixture was extracted with ethyl acetate (3×). The combined organic layers were washed with brine (3×), dried ($Na_2SO_4$) and concentrated. Silica gel FC (1:1 EtOAc/PE eluant) afforded a clean separation of the N-9 and N-7 purine isomers. The desired β-N-9 compound, 5, was obtained as an oil in 62%. $^1H$ NMR ($CDCl_3$): δ9.15 (s, H2 or H6); 8.98 (s, H2 or H6); 8.42 (d, J=2.4 Hz, H8); 6.63 (dd, J=4.0 and 16.7 Hz, H1'); 5.16 (ddd, J=3.0, 3.9 and 51.8 Hz, H2'); 4.73 (dm, J=18.1 Hz, H3'); 4.06 (q, J=4.7 Hz, H4'); 3.91 (m, H5', H5"); 0.91 (s, 9H, t-butyl); 0.10 (s, 6H, Si—$(CH_3)_2$).

9-(5'-O-tert-butyldimethylsilyl)-2'3'-dideoxy-2'-fluoro-β-D-arabinofuranosyl)- 9-H-purine (7).

Method A. Compound 5 (54 mg, 0.147 mmol) and $CS_2$ (111 mg, 1.47 mmol) were dissolved in dry DMF and cooled to 0° C. Sodium hydride (80% suspension, 10 mg) was added and the mixture was stirred at the same temperature for 30 min. Methyl iodide (208 mg, 1.47 mmol) was added via syringe and the solution was stirred for an additional 30 min. Water was added and the mixture was extracted with ether (3×). The combined organic layers were washed with brine, dried ($Na_2SO_4$) and concentrated. Following purification on silica gel, the 3'-O-xanthate, 6, was obtained in 64% yield based on recovered starting material. This compound (30 mg, 0.066 mmol) was dissolved in toluene (3 ml), a trace of AIBN was added followed by 0.1 ml of tri-n-butyltin hydride. The solution was heated to 90° C. for 10 min and the solvent was evaporated. Silica FC (2% MeOH/$CH_2Cl_2$) afforded 15 mg (65%) of the 3'-deoxy derivative 7 as a powder. Compound 6 $^1H$ NMR ($CDCl_3$): δ9.16 (s, 1H); 8.98 (s, 1H); 8.42 (d, J=3.1 Hz, H8); 6.64 (dd, J=3.0 and 21.5 Hz, H1'); 6.25 (dd, J=2.6 and 16.0 Hz, H3'); 5.28 (dd, J=3.0 and 49.8 Hz, H2'); 4.31 (q, J=4.0 Hz, H4'); 3 98 (m, H5', H5"); 2.62 (s, 3H); 0.91 (s, 9H); 0.11 (s, 6H). Compound 7: δ9.15 (s, 1H); 8.96 (s, 1H); 8.48 (d, J=2.5 Hz, H8); 6.42 (dd, 3.5 and 16.7 Hz, H1'); 5.32 (dq, $J_{2'F}$=53.5 Hz, H2'); 4.30 (m, H4'); 3.83 (d, H5'H5"); 2.59 (m, H3'); 2.44 (m, H3"); 0.92 (s, 9H); 0.11 (s, 3H); 0.103 (s, 3H). Compound 7 was used as such for the next experiment.

Method B. A mixture of t-butyl nitrite (1.12 g, 0.011 mmol) and dry THF (8 ml) was heated to reflux under an atmosphere of argon. The flask was illuminated with a 200 watt unfrosted bulb and compound 16 (200 mg, 0.55 mmol) dissolved in 2 ml of THF was added over 15 min via syringe. After 1 h at reflux TLC analysis showed disappearance of starting material and appearance of a major less polar spot, along with several very minor compounds. The solvent was evaporated and the crude residue was purified by silica flash chromatography. The major spot was isolated and determined by NMR analysis to be identical with compound 7 prepared by method A. Compound 7 was used as such for the next experiment.

9- (2',3'-dideoxy-2'-fluoro-β-D-arabinofuranosyl)-9-H-purine (1c).

Compound 7 (105 mg, 0.298 mmol) was dissolved in 80% acetic acid and heated to 90° C. for 35 min. The acid was removed in vacuo and the resulting syrup was eluted through a short silica column (5% MeOH/$CH_2Cl_2$). The nucleoside obtained was recrystallized from acetone: ether affording needles (top 93°–95° C.) of pure 1c. Yield of the hydrolysis was 88%. $^1H$ NMR ($CD_3COCD_3$): δ9.08 (s,1H); 8.90 (s, 1H); 8.66 (d, J=2.3 Hz,H8); 6.56 (dd, J=3.8 and 15.9 Hz, H1'); 5.52 (dm, $J_{2'F}$=54.4 Hz, H2');4.38 (m, H4');3.81 (m, H5', H5"); 2.78 (dddd, H3'); 2.45 (dddd, H3"). $^{13}C$ NMR ($CD_3COCD_3$): 153.2, 148.9, 145.9, 92.2, 85.2, 79.3, 64.2, 33.5. FAB-MS m/z (rel intensity), 239 ($MH^+$, 85), 121 $bH_2^+$, 100). UV ($H_2O$) $\lambda_{max}$ 261, 205 nm. $[\alpha]_D^{25}$=+38.1° (c 1.8, MeOH). Anal. ($C_{10}H_{11}FN_4O_2$) C, H, N, F.

2-methyl-9-(3',5'-di-O-benzoyl-2'-deoxy-2'-fluoro-β-D-arabinofuranosyl) adenine (8a).

2-methyladenine hemisulfate (250 mg, 1.26 mmol) was per-trimethylsilylated under argon at room temperature (acetonitrile, BSTFA) and the solvent was evaporated in vacuo. The resulting yellow oil was placed under an argon atmosphere and compound 2b (500 mg, 1.18 mmol) dissolved in dry $CH_2Cl_2$ (8 ml) was added via syringe. The solvent was removed on the rotoevaporator (40° C.), the water bath was replaced with an oil bath (100° C.) and rotation under vacuum was continued at this temperature for 45 min. The brown syrup was dissolved in $CH_2Cl_2$, filtered and concentrated. Purification on silica gel (1% MeOH/$CH_2Cl_2$-3% MeOH/$CH_2Cl_2$) afforded a mixture of isomers (71%), the desired β-N-9 nucleoside 8a being 55% of the mixture. A pure sample of 8a was obtained as a foam by repeated silica gel FC. $^1H$ NMR ($CDCl_3$): δ7.3–8.2 (m, aromatics, H8); 6.59 (dd, J=2.8 and 22.9 Hz, H1'); 5.88 (br s, $NH_2$); 5.76 (dd, J=2.7 and 17.2 Hz, H3'); 5.33 (dd, J=2.7 and 50.1 Hz, H2'); 4.79 (d, H5', H5"); 4.55 (q, J=4.1 Hz, H4'); 2.59 (s, 2-Me). At this point, it was more expedient to carry the mixture through the next step.

2-methyl-9-(2'-deoxy-2'-fluoro-β-D-arabinofuranosyl)adenine (9).

The mixture of 8a and 8b (490 mg, 1 mmol) was placed in a pressure bottle along with 10 ml of ammonia saturated methanol. The solution was allowed to stand at 5° C. for 6 h whereupon argon was bubbled through the solution. The reaction was worked up as per compound 4. Purification (FC, 5%–10% MeOH/$CH_2Cl_2$ eluant) yielded 288 mg (90%) of a 4:1 mixture of 9a and 9b. A pure sample of 9a was obtained as an oil by preparative silica gel TLC (15% MeOH/$CH_2Cl_2$). Compound 9a $^1$H NMR (D20): δ8.12 (d, J=2.1 Hz, H8); 7.22 (br s, $NH_2$); 6.35 (dd, J=4.6 and 14.6 Hz, H1'); 5.16 (dt, J=4.2 and 52.9 Hz, H2'); 4.43 (dt, J=4.0 and 19.0 Hz, H3'); 3.81 (q, J=4.6 Hz, H4'); 3.64 (br m, H5', H5"); 2.38 (s, 2-$CH_3$). $^{13}$C NMR (DMSO): 161.6, 155.6, 149.95, 139.0, 116.4, 95.4, 83.4, 81.2, 72.6, 60.4, 25.4. UV (MeOH) $\lambda_{max}$ 260, 212 nm. $[\alpha]_D^{25}$: +31.1° (c 7, MeOH). The mixture was carried through to the next step.

2-methyl-9- (5 '-O-(tert-butyldimethylsilyl) -2'-deoxy-2'-fluoro-β-D-arabinofuranosyl)adenine(10).

The 4:1 mixture of 9a and 9b (63 mg, 0.22 mmol) was dissolved in dry DMF and treated with premixed silylating agent (1 ml) as described for compound 4. After standard workup and purification on silica gel (1% MeOH/$CH_2Cl_2$) a clean separation of 5' protected nucleoside derivatives was effected, the major product being the desired compound 10 (68 mg, 77%) which was obtained as an oil. $^1$H NMR ($CDCl_3$): δ8.03 (d, J=2.8 Hz, H8); 6.56 (dd, J=3.5 and 19.2 Hz, H1'); 5.73 (br s, $NH_2$); 5.08 (ddd, J=2.2, 3.3 and 51.9 Hz, H2'); 4.67 (ddd, J=2.3, 3.7 and 17.0 Hz, H3'); 4.06 (m, H4'); 3.88 (m, H5', H5"); 2.57 (s, 2-$CH_2$); 0.89 (s, 6H, t-butyl); 0.08 (s, 3H, Si—$CH_3$); 0.07 (s, 3H, Si—$CH_3$). Anal. ($C_{17}H_{28}N_5O_3FSi$ .0.5$H_2O$) C, H, N, (C+0.5).

2-methyl-9-(5'-O-(tert-butyldimethylsilyl) -3'-O-methoxythiocarbonyl- 2'-deoxy-2 '-fluoro-β-D-arabinofuranosyl)adenine (11).

Compound 10 (60 mg, 0.15 mmol) was dissolved in dry DMF, the solution was heated to 80° C. and 1,1-thiocarbonyldiimidazole (107 mg, 0.604 mmol) was added at once. The mixture was stirred at 80° C. for 1 h and the solvent was removed in vacuo. The brown gum was dissolved in anhydrous methanol (5 ml) and this solution was refluxed for 30 min. After removing the solvent the mixture was purified by silica FC (80% EtOAc/PE eluant). Compound 11 was obtained as a powder in 70% yield (48 mg) for the two steps. $^1$H NMR ($CDCl_3$): δ8.03 (d, J=3.3 Hz, H8); 6.47 (dd, J=2.9 and 22.3 Hz, H1'); 5.93 (dd, J=2.7 and 16.0 Hz, H3'); 5.63 (br s, $NH_2$); 5.19 (dd, J=3.0 and 49.7 Hz, H2') 4.23 (m, H4') 4.10 (s, 3H, $OCH_3$); 4.04–3.87 (m, H5', H5"); 2.57 (s, 3H, 2-$CH_3$); 0.91 (s, 9H, t-butyl); 0.10 (s, 6H, Si ($CH_3$)$_2$). The compound was used without further purification in the following step.

2-Methyl-9-(5'-O-(tert-butyldimethylsilyl)-2',3'-dideoxy-2'-fluoroarabinofuranosyl)adenine (12).

Compound 11 (48 mg, 0.102 mmol) was dissolved in dry toluene and AIBN (trace) was added followed by tri-n-butyltin hydride (0.1 ml). The solution was heated to 90° C. for 10 min. The solvent was evaporated and the mixture was purified by silica FC (2% MeOH/$CH_2Cl_2$). Compound 12 was obtained as a white solid in 80% yield (31.1 mg). $^1$H NMR ($CDCl_3$): δ8.05 (d, J=2.9 Hz, H8); 6.28 (dd, J=3.2 and 19.0 Hz, H1'); 5.50 (br s, $NH_2$); 5.23 (dm, $J_{2'F}$=53.6 Hz, H2'); 4.25 (m, H4'); 3.82 (m, H5', H5"); 2.57(s, 2-$CH_3$); 0.92 (s, 9H, t-butyl); 0.10 ( s, 3H, Si—$CH_3$); 0.09 ( s, 3H, Si—$CH_3$). The compound was used directly in the next step.

2-methyl-9-(2', 3'-dideoxy-2'-fluoro-β-D-arabinofuranosyl)adenine (1d).

Compound 12 (31.1 mg, 0.082 mmol) was dissolved in 4 ml of acetic acid. To this solution was added 1 ml of water with stirring and the flask was heated to 90° C. for 1 h. The acid was removed in vacuo and the resulting gum purified first by silica FC (5% MeOH/$CH_2Cl_2$) and then by reverse phase $C_{18}$ chromatography eluting with a gradient of water10% MeOH/$H_2O$. The desired nucleoside was recrystallized from acetone affording needles (mp 237°–239° C.) in 87% yield (19 mg). $^1$H NMR ($CD_3COCD_3$): δ8.08 (d, J=2.3 Hz, H8); 6.48 (br s, $NH_2$); 6.32 (dd, J=3.9 and 16.6 Hz, H1'); 5.42 (dm, $J_{2'F}$=54.5 Hz, H2'); 4.57 (m, H4'); 4.29 (m, H5', H5"); 2.64 (m, H3'); 2.42 (m, H3"); 2.41 (s, 2-$CH_3$). $^{13}$C NMR ($D_2O$): 165.2, 157.4, 151.5, 143.0, 118.4, 93.7, 87.3, 80.5, 65.8, 34.7, 26.4. FAB-MS m/z (rel intensity), 268 ($MH^+$, 100), 150 ($bH_2^+$, 53); accurate mass m/z 268.1180 ($MH^+$, calcd 268.1210). UV ($H_2O$) $\lambda_{max}$ 260, 208 nm. $[\alpha]_D^{25}$:+46.1° (c 3.1, $H_2O$). Anal. ($C_{11}H_{14}O_2FN_5$) C, H, N.

8-Methyl-9-(2',3'-dideoxy-2'-fluoro-β-D-arabinofuranosyl)adenine (1h).

A solution of diisopropylamine (260 mg, 2.72 mmol) in dry THF (3 ml) was cooled to –78° C. n-Butyl lithium (1.35 ml of a 1M solution) was added dropwise via syringe and the solution was stirred at the same temperature for 15 min. Compound 16 (Marquez, V. E. et al. *J. Med. Chem.* 1990, 33, 978) (200 mg 0.544 mmol) dissolved in THF (3.5 ml) was next added under a positive pressure of argon and the solution was stirred for an additional 20 min. Methyl iodide (0.9 ml, 1.36 mmol) was added and after 15 min at –78° C. the reaction was quenched with acetic acid. The solution was warmed to room temperature and diluted with ether. The organic layer was washed sequentially with water, saturated $NaHCO_3$ solution and brine, dried over $Na_2SO_4$ and evaporated. After purification on silica gel, a mixture of the desired 8-methyl derivative and several minor byproducts was isolated (134 mg). This was treated with 80% acetic acid/water at 90° C. for 40 min and the acid was evaporated. Purification by prep TLC (silica, 10% $CH_2OH/CH_2Cl_2$, eluant) followed by semi-preparative HPLC ($C_{18}$ silica, 15% acetonitrile/water eluant) afforded pure 1h (30 mg) which recrystallized from acetone as a white solid (mp 208°–209° C.) in 22% overall yield. $^1$H NMR ($D_2O$): δ7.86 (s, H2); 6.08 (dd, J=3.7 and 20.2 Hz, H1'); 5.21 (dm, $J_{2'F}$=54.5 Hz, H2'); 4.24 (m, H4'); 3.76 (dd, J=2.5 and 12.4 Hz, H5'); 3.63 (dd, J=4.8 and 12.4 Hz, H5"); 2.60 (m, H3'); 2.42 (s, 8-Me); 2.16 (m, H3"). $^{13}$C NMR ($D_2O$): 156.6, 153.9, 153.8, 152.1, 119.3, 94.5, 89.2, 80.4, 65.5, 35.0, 17.2. FAB-MS m/z (rel intensity), 268 ($MH^+$, 100), 150 ($bH_2^+$, 35). UV ($D_2O$) $\lambda_{max}$ 261, 209 nm. $[\alpha]_{D25}$= +37° (c 2.0, MeOH). Anal. ($C_{11}H_{14}FN_5O_2$) C, H, N, F.

2-Methyl-$N^6$-benzoyl-9-(2'-deoxy-5'-O-(tert-butyldimethylsilyl-2'-fluoro-β-D-arabinofuranosyl)adenine (13).

Benzoyl chloride (0.5 ml, 1.57 mmol) was added to a solution of compound 10 (58 mg, 0.157 mmol) in dry pyridine (3 ml) previously cooled to 0° C. After 2 h at this temperature the reaction was quenched with saturated sodium bicarbonate solution and the resulting mixture was extracted with ethyl acetate (3×). The combined organic layers were washed with water and brine, dried ($Na_2SO_4$) and concentrated to a gum. The crude dibenzoate was dissolved in 4 ml of pyridine:methanol:water (65:30:5), cooled to 0° C. and treated with 2 ml of 2N NaOH solution. After 30 min at this temperature solid $NH_4Cl$ was added followed by water and the aqueous layer was extracted with ethyl acetate as described above. Chromatography on silical gel afforded 58 mg (78%) of the monobenzoate 13 as an oil. 1H NMR ($CDCl_3$): δ8.95 (br s, NH); 8.20 (d, J=2.7 Hz, H8); 8.04 and 7.55 (m, aromatics); 6.59 (dd, J=3.6 and 19.0 Hz, H1'); 5.11 (ddd, $J_{2',F}$=51.6 Hz, H2'); 4.67 (dm, $J_{3',F}$=17.8 Hz, H3'); 4.03 (m, H4'); 3.87 (m, H5', H5"); 2.75 (s, 2-CH$_3$); 0.90 (s, 9H, t-butyl); 0.09 (s, 6H, Si—(CH$_3$)$_2$). This compound was used directly in the next step.

2,N$^6$-dimethyl-N$^6$-benzoyl-9-(5'-O-(tert-butyldimethylsilyl)-3'-O-xanthyl-2'deoxy-2'-fluoro-β-D-arabinofuranosyl)adenine (14).

A solution of compound 13 (80 mg, 0.17 mmol) and carbon disulfide (129 mg, 1.7 mmol) in dry DMF (4 ml) was cooled to 0° C. and sodium hydride (11 mg of an 80% slurry in mineral oil) was added at once. The bright red mixture was stirred at 0° C. for 30 min. Methyl iodide (241 mg, 1.7 mmol) was added via syringe and the resulting yellow solution was stirred for an additional 20 min. Water was added and the solution was extracted with ether (3×). The combined ether layers were washed with brine (3×), dried (Na$_2$SO$_4$) and concentrated. Silica FC yielded 63.8 mg (65.4%) of the desired N-methyl-3'-xanthate as an oil along with 20% of a by product believed to be the N1-methylated compound. $^1$H NMR (CDCl$_3$): δ8.12 (d, J=3.1 Hz, H8); 7.1–7.5 (m, aromatics); 6.49 (dd, J=2.9 and 22.0 Hz, H1'); 6.22 (dd, J=2.7 and 16.5 Hz, H3'); 5.20 (dd, J=3.1 and 49.8 Hz, H2'); 4.25 (m, H4'); 3.95 (m, H5', H5"); 3.79 (s, N—CH$_3$); 2.62 (s, S—CH$_3$); 2.47 (s, 2-CH$_3$); 0.90 (s, t-butyl); 0.09 (s, Si—(CH$_3$)2). The compound was used as such for the next step.

2,N$^6$-Dimethyl-N$^6$-benzoyl-9-(5'-O-(tert-butyldimethylsilyl)- 2',3'-dideoxy-2'-fluoro-β-D-arabinofuranosyl)adenine (15).

A toluene solution (3 ml) of compound 14 (63 mg, 0.109 mmol) containing AIBN (trace) and tri-n-butyltin hydride (95 mg, 0.327 mmol) was heated to 90° C. for 10 min. The solvent was evaporated and the mixture purified on silica gel (2% MeOH/CH$_2$Cl$_2$) affording 45 mg (86.6%) of the 3' deoxy product 15 as an oil. $^1$H NMR (CDCl$_3$): δ8.15 (d, J=2.7 Hz, H8); 7.1–7.5 (m, aromatics); 6.28 (dd, J=3.2 and 18.4 Hz, H1'); 5.22 (dm, $J_{2',F}$=53.6 Hz, H2'); 4.23 (m, H4'); 3.79 (d, H5', H5"); 3.77 (s, N—CH$_3$); 2.3– 2.6 (m, H3', H3"); 2.44 (s, 2-CH$_3$); 0.89 (s, t-butyl); 0.07 (s, Si(CH$_3$)$_2$). This compound was used directly in the following final reaction.

2,N$^6$-Dimethyl-9-(2',3'-dideoxy-2'-fluoro-β-D-arabinofuranosyl)adenine (1e).

Compound 15 (45 mg, 0.957 mmol) was treated with a saturated solution of ammonia in methanol in a pressure bottle at room temperature. After 4 h argon was bubbled through the solution and the methanol was evaporated. The resulting oil (15a) was dissolved in THF (3 ml) and treated with tetrabutylammonium fluoride (0.1 ml of a 1.0M solution in THF). After 5 min at 25° C. the solvent was evaporated and the oil was purified by silica prep TLC (10% MeOH/CH$_2$Cl$_2$) and reverse phase C$_{18}$ chromatography (gradient of water-20% MeOH/H$_2$O ). The desired nucleoside 1e was recovered as a glass in 78% (20 mg) over the two steps. $^1$H NMR (CD$_3$COCD$_3$): δ8.05 (d, J=2.2 Hz, H8); 6.75 (br s, N$_H$); 6.32 (dd, J=3.9 and 16.5 Hz, H1'); 5.42 (dm, $J_{2',F}$=54.6 Hz, H2'); 4.63 (br s, OH); 4.29 (m, H4'); 3.75 (m, H5', H5"); 3.11 (br s, N—CH$_3$); 2.3–2.8 (2 dddd, H3', H3"); 2.43 (s, 2-CH$_3$). $^{13}$C NMR (CD$_3$COCD$_3$): 162.8, 156.1, 155.9, 139.6, 92.3, 85.6, 78.9, 64.2, 33.4, 29.4, 26.0. FAB-MS m/z (rel intensity), 282 (MH$^+$, 100), 164 (bH$_2^+$, 64). UV (H$_2$O) $\lambda_{max}$ 267, 212 nm. $[\alpha]_D^{25}$: +37.8° (c 6, H$_2$O). Anal. (C$_{12}$H$_{16}$N$_5$O$_2$F.0.8H$_2$O) C,H,N (N–0.7).

6-Amino-9-[5-O-tert-butyldimethylsilyl)-2,3-dideoxy-2-fluoro-β-D-threo-pento-furanosyl]-9H-purine (16).

Compound 16 was prepared as previously described (Marquez, V. E. et al. *J. Med. Chem.* 1990, 33, 978).

6-Chloro-9-(2',3'-dideoxy-2-fluoro-β-D-arabinofuranosyl)purine (1i).

Compound 16 (216 mg, 0.59 mmol) was suspended in dry CCl$_4$ (7 ml) and 1.34 ml (11.8 mmol) of freshly distilled t-butyl nitrite was added. The mixture was heated to 80° C. and illuminated with a 200 Watt unfrosted bulb maintained one inch from the reaction flask. After 12 h the reagents and solvent were evaporated in vacuo. The residue was dissolved in 10% CH$_3$OH/CH$_2$Cl$_2$, a small amount of celite was added and the solution was filtered through sodium sulfate and evaporated. Chromatography on silica gel (CH$_2$Cl$_2$ then 2% CH$_3$OH/CH$_2$Cl$_2$, eluant) afforded 85 mg (37%) of the 5'-protected-6-chloro derivative. This was treated with 80% acetic acid at 85° C. for 30 min. The acid was evaporated and the residue was purified on a C$_{18}$ silica extraction column (Baker, 2.5% CH$_3$OH/H$_2$O eluant) yielding 37 mg (62%) of the target nucleoside 1i. An analytically pure sample was obtained by a second chromatography on an Altex C$_{18}$ HPLC column employing 20% CH$_3$CN/H$_2$O. $^1$H NMR (CD$_3$COCD$_3$): δ8.78 (d, J=2.2 Hz, H8); 8.72 (s, H2); 6.55 (dd, J=3.4 and 15.0 Hz, H1'); 5.59 (dm $J_{2',F}$=54.3 Hz, H2'); 4.38 (m, H4'); 3.82 (br AB, H5', 5"); 2.72 (m, H3'); 2.46 (m, H3"). $^{13}$C NMR (D$_2$O): δ151.9, 151.1, 150.2, 146.4, 91.5, 78.5, 63.3, 32.3. FAB-MS m/z (rel intensity), 273 (MH$^+$, $^{35}$Cl, 100), 239 (MH—Cl+H, 29, 155 (bH$_2^+$,$^{35}$Cl, 70); accurate mass m/z 273.0561 (MH$^+$ calcd 273.0555). UV (CH$_3$OH): $\lambda_{max}$ 260, 252 (inflection), 208. $[\alpha]_D$=+55.7 (C 1.4). Anal. (C$_{10}$H$_{10}$N$_4$O$_2$ClF) C, H, N.

N$^6$-Benzoyl-9-(5'-O-(tert-butyldimethylsilyl)-2,3'-dideoxy-2'-fluoro-β-D-arabinofuranosyl) adenine (17).

Compound 16 (200 mg, 0.545 mmol) was treated under identical conditions as in the preparation of compound 13. After workup and purification by silica FC (2% MeOH/CH$_{Cl2}$) 206 mg (77.8%) of the monobenzoate 17 was obtained as an oil along with approximately 10% of the dibenzoyl intermediate. $^1$H NMR(CDCl$_3$): 9.11 (br s, NH); 8.79 (s, H2); 8.35 (d, J=2.6 Hz, H8); 6.40 (dd, J=3.4 and 17.7 Hz, H1'); 5.31 (dm, $J_{2',F}$=53.5 Hz, H2'); 4.32 (m, H4'); 3.85 (d, H5', H5"); 2.57 (m, H3'); 2.43 (m, H3"); 0.92 (s, t-butyl); 0.11 (s, Si—CH$_3$); 0.10 (s, Si—CH$_3$). This compound was carried to the next step.

N$^6$-Methyl-N$^6$-benzoyl-9-(5'-O-(tert-butyldimethylsilyl)-2', 340 -dideoxy-2'-fluoro-β-D-arabinofuranosyl)adenine (18).

This was prepared in an identical manner to compound 14. After workup and purification, 100 mg (47%) of the desired N$^6$ methyl derivative 18 was recovered as an oil along with 38 mg (18%) of what was most likely the N1-methyl derivative. $^1$H NMR (CDCl$_3$): δ8.51 (s, H2); 8.32 (d, J=2.6 Hz, H8); 7.1–7.5 (m, aromatics); 6.31 (dd, J=3.4 and 17.4 Hz, H1'); 5.25 (dm, $J_{2',F}$=53.7 Hz, H2'); 4.26 (m,H4'); 3.80 (s, N—CH$_3$); 3.79 (m, H5', H5"); 2.53 (m, H3'); 2.39 (m, H3"); 0.90 (s, 9H, t-butyl); 0.10 (s, 6 H, Si—(CH$_3$)$_2$). This compound was used directly in the next step.

N$^6$-Methyl-9-(2'3'-dideoxy-2'-fluoro-β-D-arabinofuranosyl)adenine (1f).

Compound 18 (100 mg, 0.206 mmol) was debenzoylated as per the other benzoates (ammonia saturated methanol, pressure bottle, 0° C. for 4 h then room temperature for 2 h) affording after typical workup and FC on silica the N$^6$-methyl-5'-O-protected derivative 19 in >90% yield. This was dissolved in 80% glacial acetic acid and heated to 90° C. for 20 min. After evaporation of the acid and preparative TLC on silica (10% MeOH/CH$_2$Cl$_2$) 45 mg (82% for two steps) of the desired nucleoside if was obtained as a glass. Compound 19 $^1$H NMR (CDCl$_3$): δ8.38 (s, H2); 8.07 (d J=2.7 Hz, H8); 6.29 (dd, J=3.2 and 18.4 Hz, H1'); 6.01 (br s, NH); 5.24

(dm, $J_{2',F}$=53.7 Hz, H2'); 4.25 (m, H4'); 3.81 (d, H5', H5"); 3.19 (br d, J=4.6 Hz, N—CH$_3$); 2.53 (m, H3'); 2.36 (m, H3"); 0.91 (s, t-butyl); 0.09 (s, Si—CH$_3$); 0.08 (s, Si—CH$_3$). Compound 1f $^1$H NMR (D$_2$O): δ8.25 (br s, H2); 8.18 (d J=2.3 Hz, H8); 7.01 (br s, NH); 6.38 (dd, J=3.8 and 16.5 Hz, H1'); 5.42 (dm, $J_{2',F}$=54.4 Hz, H2'); 4.59 (br s, OH): 4.31 (m, H4'); 3.78 (br m, H5', H5"); 3.11 (br s, N—CH$_3$); 2.30–2.83 (2 dddd, H3', H3"). $^{13}$C NMR (D$_2$O): 156.8, 154.5, 148.9, 142.4, 120.0, 93.5, 87.1, 80.5, 65.9, 34.8, 29.7. FAB-MS m/z 268 (MH$^+$, 100), 150 (bH2$^+$, 30). UV (H$_2$O): 265, 211 nm. [α]$_D^{25}$: +56.8° (c 1.9, MeOH). Anal. (C$_{11}$H$_{14}$O$_2$FN$_5$.0.7 H$_2$O) C, H, N.

N$^6$-benzoyl-9-(2',3'-dideoxy-2'-fluoro-β-D-arabinofuranosyl)adenine (1g).

Compound 17 (49 mg, 0.104 mmol) was hydrolyzed with 80% acetic acid at 90° C. for 30 min. After evaporation of the acid and recrystallization from ether/CH$_2$Cl$_2$, the desired nucleoside 1g was obtained in 68% yield (23.4 mg), mp 187°–189° C. $^1$H NMR (CD$_3$COCD$_3$): δ9.97 (br s, NH); 8.65 (s, H2); 8.51 (d, J=2.3 Hz, H8); 6.52 (dd, J=3.8 and 16.1 Hz, H1'); 5.52 (dm, $J_{2',F}$=54.4 Hz, H2'); 4.36 (m, H4'); 4.30 (t, J=6.0 Hz, OH); 3.80 (m, H5', H5"); 2.3–2.9 (2 dddd, H3', H3"). $^{13}$C NMR (CD$_3$COCD$_3$): 168.9, 152.3, 151.9, 149.5, 144.5, 133.7, 133.0, 129.2, 128.4, 123.5, 91.8, 85.3, 78.7, 63.6, 32.6. FAB-MS m/z (rel intensity), 358 (MH$^+$, 100), 240 (bH$_2^+$, 61), 105 (93). UV (MeOH) λ$_{max}$ 278, 231 (sh), 205 nm. [α]$_D^{25}$: 31.7° (c 1.7, MeOH). Anal. (C$_{17}$H$_{15}$O$_3$FN$_5$. 0.2 H$_2$O) C, H, N, F.

9-(2',3'-Dideoxy-2'-fluoro-β-D-arabinofuranosyl)adenine-1-oxide (21).

Compound 1a (225 mg, 0.89 mmol) was dissolved in 8 ml of acetic acid and 1.5 ml of 30% solution of hydrogen peroxide was added. The mixture was stirred at room temperature for 5 days, the flask was cooled to 0° C. and 10% palladium on carbon was added. After stirring for 30 min, the mixture was filtered through celite and concentrated. The crude syrup was purified by flash chromatography on C$_{18}$ silica, eluting with a gradient of water-5% MeOH/H$_2$O, affording 132 mg of product. This was crystallized from 95% EtOH affording 101 mg (42%) as needles, mp, dec>230° C. $^1$H NMR (DMSO-d$_6$): δ8.56 (s, H2); 8.45 (d, J=2.0 Hz, H8); 6.30 (dd, J=3.9 and 15.1Hz, H1'); 5.43 (dm, $J_{2',F}$=54.6 Hz, H2'); 5.04 (t, J=5.8 Hz, 5'-OH); 4.17 (m, H4'); 3.61 (br s, H5', H5"); 2.54 (m, H3'); 2.24 (m, H3"). $^{13}$C NMR (DMSO-d$_6$): 148.3, 143.4, 142.5, 141.4, 117.9, 91.5, 83.5, 78.0, 62.7, 32.2. FAB-MS m/z (rel intensity), 270 (MH$^+$, 48), 254 (MH—O$^+$, 100), 152 (bH$_2^+$, 16), 136 (bH$_2$—O$^+$, 62). UV λmax (H$_2$O): 232, 263. [α]$_D^{25}$: +12.2° (c=1.0, MeOH). Anal. (C$_{10}$H$_{12}$N$_5$O$_2$F) C, H, N, F.

The compounds of interest were prepared via a common carbohydrate precursor, 1,3,5-tri-O-benzoyl- 2'-fluoro-α-D-ribofuranose 2a. (Tann, C. H. et al. *J. Org. Chem.*, 1985, 50, 3644) Anomeric bromination with 30% HBr/acetic acid followed by condensation of the resulting sugar 2b with the appropriate pertrimethylsilylated base afforded the protected nucleosides 3 and 8 as intermediates in the synthesis of target compounds 1c, 1d and 1e (Scheme 1). Fusion of 2b with purine gave mainly 3a along with minor percentages of the β-N-7 and α-N-9 nucleosides, 3b and 3c. The analogous coupling of 2-methyladenine gave 8a as the major product along with 25% of the β-N-9 compound 8b and very minor amounts of N-7 and N-6 alkylated bases.

Ammonolysis of the acyl groups with ammonia-saturated methanol in a pressure bottle at 4° C. afforded the 2'-fluoro-2'-deoxy nucleosides 4a and 9a in high yield.

The stereochemistries of the major products were assigned by NMR coupling constants based on precedent (Herdewijn, P. et al. *J. Med. Chem.* 1987, 30, 2131) and the regiochemistries (N9 versus N-7) by UV (Albert, A. in "Synthetic Procedures in Nucleic Acid Chemistry", W W Zorbach and R. S. Tipson, eds. 1973, Chapter 2) 71 and one dimensional nOe difference (ID nOe) spectra. In general, $^3J_{1',2'}$ in β-nucleosides with a 2'-ara substituent is in the range of 3–4 Hz whereas the α-nucleosides show extremely small or no coupling between the 1'- and 2'- protons. Also characteristic of β-D-2'-ara-fluoro nucleosides of the purine series is the small but finite coupling (1–3 Hz) of the 2'-fluorine atom to H8 of the base (Herwewijn, P. et al *Nucleosides and Nucleotides,* 1989, 8, 65), $^5J_{8,F}$=2.5 Hz in these compounds). Distinguishing the N-7 and N-9 regioisomers of the 2-methyladenine derivatives 9a and 9b was based on the significant difference in the UV maxima of alkyl substituted adenines. (Albert, A. in "Synthetic Procedures in Nucleic Acid Chemistry", W. W. Zorbach and R. S. Tipson, eds. 1973, Chapter 2) This correlation was used previously to distinguish the N-7 and N-9 isomers of compound 1a (Marquez, V. E. et al. *J. Med. Chem.* 1990, 33, 978) Since the methyl group at the 2-position has little effect on the position of the UV maxima, compound 9a whose UV maximum was centered at 260 nm was assigned the N-9 structure. In the case where unsubstituted purine is the base (compounds 4a and 4b), the assignment of regiochemistry based on a similar argument is ambiguous (maxima of 4a and 4b are 261 and 264 nm, respectively). The $^1$H NMR spectrum of 4a was virtually identical to 4b except for a subtle difference in the chemical shifts of the H1' protons. When H1' of 4b was irradiated in a 1D nOe experiment, positive enhancements were observed at H6 and H8 in addition to the expected enhancement at H2'. When a similar experiment was performed on compound 4a, a positive nOe was observed on only one base proton (H8). These data suggest the regiochemistries of 4a and 4b to be N-9 and N-7, respectively. This qualitative assessment was confirmed by conversion of the known 5'-protected adenosine derivative 16 to the corresponding nebularine analogue 7 by reductive deamination (Nair, V. & Richardson, S. G. *J. Org. Chem.* 1980, 45, 3969) (Scheme 2).

Selective 5'-protection of compounds 4a and 9a yielded the alcohols 5 and 10, while monobenzoylation (Jones, R. A. in "Oligonucleotide Synthesis", M. Gait ed 1984 chapter 2) of 10 gave 13, all in high yield (Scheme 1). Reductive deoxygenation of the 3'-hydroxyl groups of compounds 5 and 10 to produce 7 and 12 proceeded without incident through the methyl xanthate 6 and the methoxythiocarbonyl derivative (Sanghvi, Y. S. et al. *Nucleosides and Nucleotides,* 1987, 6, 761), 11, respectively. Acid catalyzed deprotection of 7 and 12 gave the corresponding targets, 1c and 1d. Preparation of the xanthate of 13 produced the N$^6$-methylated product, 14, the precursor of nucleoside 1e. Radical deoxygenation of 14 and sequential deblocking of the resulting product 15, via 15a, afforded the desired 2,N$^6$-dimethyladenine analogue, 1e.

Compounds 1f, 1g and 1h were prepared from the known 5'-O-(t-butyl-dimethylsilyl)-2',3'-dideoxy nucleoside, 16 (Marquez, V. E. et al. *J. Med. Chem.* 1990, 33, 978) (Scheme 2). Dibenzoylation of 16 followed by NaOH cleavage (Jones, R. A. in "Oligonucleotide Synthesis", M. Gait, ed., 1984, chapter 2) to the monobenzoyl derivative and desilylation afforded the N$^6$-benzoyl nucleoside 1g. Compound if was prepared from 17 via methylation and sequential deblocking of the N-and O-protecting groups as for 1e. Direct lithiation (Hayakawa, H. et al. *J. Heterocyclic Chem.*, 1989, 16, 189) of the 8-position of 16, followed by quenching with methyl iodide and deprotection, gave the 8-substituted derivative 1h in low to moderate yield. A significant amount of the olefin, 20, was formed from base-catalyzed elimination of hydrofluoric acid. Loss of the absorption for H1' and the appearance of an olefinic multiplet at 5.58 ppm which couples strongly to the H3' methylene in the $^1$H NMR provided evidence of structure 20.

The 6-chloro derivative 1i was prepared via compound 16 by the method of Nair (Nair, V. & Richardson, S. G. *J. Org. Chem.* 1980, 45, 3969) (Scheme 2). Direct replacement of the 6-amino group with chlorine proceeds in modest but acceptable yield (ca. 50%). Compound 1a was oxidized to the 1-oxide, 21 by the action of hydrogen peroxide in acetic acid.

EXAMPLE 2

Partition Coefficients

Molecules with a 100-fold range of lipophilicities were designed within the 2'-fluoropurine ddN series (Table I). Octanol/pH 7.0 buffer partition coefficients were determined using a newly developed microscale method. The $N^6$-benzoyl compound, 1g, was the most lipophilic compound produced in this series with an octanol/pH 7.0 buffer partition coefficient (P) of 5.4 (log P 0.73). The 1-oxide of ddA, 21, was the most hydrophilic compound synthesized with a P of 0.04 (log P -1.38). Lipophilicities of these two compounds are five times greater and 27 times less, respectively, than AZT. The other compounds synthesized had intermediate P values. The addition of a methyl group normally increases the log P value of a compound by about 0.5. (Craig, P. *J. Med. Chem.* 1971, 14, 680) In the dideoxynucleoside series, however, the lipophilicity constant (pi value) for a methyl group proved to be somewhat less, 0.3–0.4 (Table I).

TABLE I

Octantol-Water Partition Coefficients and Chromatographic Properties of 2',3'-Dideoxy Nucleosides

| Compound | Log P[a] | NPLC Mobile Phase[b] | $\lambda_{max}$[c] (nm) |
|---|---|---|---|
| 21 | -1.38 ± 0.06 | B | 231,260 |
| ddC | -1.33 ± 0.01 | A | 271 |
| ddI | -1.24 ± 0.03 | C | 249 |
| 1b | -1.21 ± 0.02 | C | 247 |
| 1c | -0.40 ± 0.01 | D | 261 |
| ddA | -0.29 ± 0.01 | D | 260 |
| 1a | -0.18 ± 0.01 | D | 259 |
| AZT | 0.05 ± 0.01 | F | 266 |
| 1h | 0.10 ± 0.01 | D | 260 |
| 1d | 0.12 ± 0.02 | D | 260 |
| 1f | 0.27 ± 0.01 | E | 265 |
| 1i | 0.32 ± 0.02 | F | 264 |
| 1e | 0.64 ± 0.01 | F | 265 |
| 1g | 0.70 ± 0.02 | F | 280 |

[a]Mean ± standard deviation of three independent determinations
[b]The following mobile phases were used at 1.0 ml/min with a 4.6 × 250 mm 5-μm Ultrasphere ODS column: A) 4%, B) 7%, C) 10%, D) 12%, E) 15% or F) 20% CH$_3$CN in pH 7.0, 0.01M phosphate buffer. ALL dideoxynucleosides had a retention time of 4–9 min under the above conditions.
[c]Wavelength determined on-the-fly in HPLC mobile phase.

EXAMPLE 3

Anti-HIV Activity in vitro

The various monomethyl analogues (1d, 1f, 1h) were prepared in an attempt to produce an increase in lipophilicity without adversely affecting the anti-HIV activity of the parent compound, 1a. The N6-methyl analogue (1f) (Driscoll, J. et al. Vth Internat. Conf. on AIDS, Montreal, 1989, M.C.P. 107) was the only monomethyl compound with any in vitro activity (under the in vitro test conditions), and that activity was reduced relative to 1a (Table II). Activity with the corresponding non-fluorinated compound had been reported earlier by Chu and co-workers (Chu, C. K. et al. *Proc. 197th Am. Chem. Soc. Meeting*, Miami, 1989, Medicinal Chemistry, 89), and the activity of 1f against HIV in peripheral blood mononuclear cells was recently reported by the same group (Chu, C. K. et al. *J. Med. Chem.* 1990, 33, 1553). Compound 1e is the 2-methyl analogue of 1f. As with 1d, the methyl group in the 2-position abolished activity. Substitution at $N^6$ with a benzoyl group (1g) resulted in the preservation of modest activity. Generation of the 1-oxide (21) of the parent compound, 1a, or removal of the 6-amino group to produce the nebularine analogue, 1c, abolished activity. The 6-chloro analogue (1i) however, provided ca. 50% protection to HIV-infected ATH8 cells. This finding, as well as the activity found for 1f, demonstrated that the 6-substituted compounds were perhaps being converted to an active metabolite. A reasonable explanation was that adenosine deaminase (ADA) catalyzed the hydrolysis of these compounds to the known active inosine analogue, 1b, (Scheme 3). The ATH8 cells and the incubation medium (which contains 15% fetal calf serum) contain some ADA which can act on the ddN during the seven day in vitro anti-HIV test. For this reason, it was decided to quantitate how rapidly the N6-methyl compound, 1f, was converted to 1b by ADA, and determine if this property could be used to advantage with prodrugs of ddI, ddG, and their 2'-fluoro analogues.

TABLE II

Effect of 2'-Deoxycoformycin on the Anti-HIV Activity of 2',3'-Dideoxyadenosine Analogues in ATH-8 Cells[a]

| Compound | dCF (5 μm) | Concentration μM | % Protection | % Toxicity |
|---|---|---|---|---|
| 1a | − | 0,20,50 | 0,70,84 | 0,0,0 |
|    | + | 0,20,50 | 0,68,48 | 11,17,54 |
| 1f | − | 0,5,10,20,50,100 | 0,13,24,32,37,27 | 0,0,0,0,6,44 |
|    | + | 0,5,10,20,50,100 | 0,1,2,0,0,0 | 11,3,7,0,46,70 |
| 1g | − | 0,5,20,50,100 | 0,8,30,29,21 | 0,2,0,0,8 |
| 1i | − | 0,10,20,50,100 | 0,48,57,53,35 | 0,5,26,46,52 |
|    | + | 0,10,20,50,100 | 3,15,11,14,17 | 14,49,58,56,72 |
| ddA | − | 10 | 100 | 0 |
|     | + | 10 | 86 | 22 |
| ddI | − | 20 | 100 | 0 |

[a]ATH8 cells were exposed to HIV-1/III$_B$ per cell for 1 hr and cultured in the presence of various concentrations of each compound. On day 8, the total viable cells were counted. Orders of numbers in the column for concentrations correspond to the orders of numbers in other columns.

EXAMPLE 4

Adenosine Deaminase

Kinetic data already available indicated that the deamination of N6-methyl adenosine riboside analogues was slow. (Chassy, B. M. & Suhadolnik, R. J. *J. Biol. Chem.* 1967, 2.42, 3655; Baer, H. P. et al. *Arch. Biochem. Biophys.* 1968, 123, 172) Reaction of the $N^6$-methyl analogue, 1f, with ADA as the isolated enzyme (0.7 U/mL) at 37° C. showed that a hydrolysis reaction occurred at a rate substantial enough to be easily quantified (FIG. 1, $t_{1/2}$=3.0 h), but which was 135 times slower than 1a (FIG. 1, inset). It was also established that the corresponding inosine analogue, 1b, was the product formed, and that the rate of formation of 1b corresponded to the rate of disappearance of 1f (FIG. 1). Dideoxyadenosine and its 2'-fluoro analogue, 1a, were deaminated at much faster rates ($t_{1/2}$=5 and 80 sec, respectively) under these conditions (FIG. 1, inset). As expected (Frederiksen, S. & Rasmussen, A. H. Cancer. Res. 1967, 27, 385; Williamson, J. & Scott-Finnigan, T. J. Antimicrob. Agents Chemother. 1978, 13, 735), no deamination was observed under the same conditions with the N-oxide, 21. Similarly, the $N^6$-benzoyl compound, 1g, was unaffected by ADA.

Because of the ubiquitous nature of ADA in vivo, it occurred to us that the ADA-catalyzed hydrolysis of 6-substituted dideoxypurine nucleoside analogues might possibly be used to advantage in anti-AIDS therapy in general, and in CNS therapy, in particular. The ADA reaction might be of general utility if the proper hydrolysis rate could be achieved for a compound which was converted into an active material, eg. 1b. In addition, if a compound could be designed which was catabolized slowly enough by ADA in the peripheral circulation to allow transport into the CNS, but fast enough by ADA in the CNS to provide therapeutic concentrations of an active, more hydrophilic inosine analogue, then a drug delivery system could be available which provided enhanced CNS prodrug entry with reduced therapeutic drug exit. This would be a variation on the CNS "locked-in" effect of very polar molecules which is a part of the dihydropyridine CNS prodrug system developed by Bodor and coworkers (Pop, E. et al. J. Med. Chem. 1989, 32, 1774) and is important since it is generally thought that compounds which enter the CNS easily also exit easily (Palomino, E. et al J. Med. Chem. 1990, 33, 258). The reported values for ADA in the CNS are somewhat variable, but it appears clear that certain CNS diseases, especially meningeal tuberculosis, greatly increase ADA activity relative to normal controls. (Hankiewicz, J. & Lesniak, M. Enzymologia 1972, 43, 385; Piras, M. A. & Gakis, C. Enzyme 1972/73, 14, 311; Malan, C. et al J. Trop. Med. Hygiene 1984, 87, 33; Norstrand, I. F. et al. Enzyme 1984, 32, 20) Whether AIDS causes a similar effect on ADA CNS levels is, however, presently unknown.

Since it is reported that ADA hydrolyzes a number of groups other than the amino function in the 6-position of purine nucleosides (Chassy, B. M. & Suhadolnik, R. J. J. Biol. Chem. 1967, 242, 3655; Baer, H. P. et al. Arch. Biochem. Biophys. 1968, 123, 172; Simon, L. N. et al. Biochemistry 1970, 9, 573; Maguire, M. H. & Sim, M. K. Eur. J. Biochem. 1971, 23, 22), the 6-chloro derivative, 1i, also appeared to be an attractive target, since the pi value for an aromatic chlorine is +0.71. This should result in a compound, 1i, with a predicted log P value of 0.31 based on 1c. Table I shows that this is the case. Another reason for the interest in 1i is the recently demonstrated anti-HIV activity of the non-fluorosugar analogues of the 2',3'-dideoxy-6-halopurines in multiple CD4+ cell systems, including the ATH8 system (Shirasaka, T. et al Proc. Nat. Acad. Sci. (USA), in press). Because of the reproducible, albeit unspectacular, activity found for 1i and 1f (Tabe II), it was decided to examine the role of ADA by determining the enzyme kinetics for the hydrolysis of several active 2'-fluoro analogues (1a, 1f and 1i, Scheme 3) relative to the non-fluorinated dideoxynucleoside, ddA.

As seen in Table III, there are significant variations in both the binding affinities ($K_M$) and the maximum reaction velocities ($v_{max}$) among the 2'-fluoro analogues and between ddA. None of the 2'-fluoro dideoxynucleosides bound as tightly or reacted as rapidly with ADA as the parent compound, ddA. Therefore, large differences thus exist in the measured relative rates of ADA hydrolysis determined at 50 µM substrate for these compounds as compared to ddA.

Both the 6-chloro (1i) and 6-methylamino (1f) analogues are hydrolyzed much more slowly (ca. 1700 and 2500 times slower, respectively) than ddA. While if was bound to ADA about 70 times tighter than 1i, its $v_{max}$ was 50 times slower resulting in the measured relative rates being fairly similar. Compound 1a was hydrolyzed 17 times slower than ddA, which compares with a value of ca. 10 times slower determined previously under slightly different conditions. (Masood, R. et al Mol. Pharmacol. 1990, 37, 590) Relative rates were measured using 50 µM substrate (Table III), since this concentration produced an anti-HIV protective effect with the compounds shown in Table II. Preliminary experiments indicate that the ADA level in media alone (no ATH8 cells) is more than 1000 times lower than the 0.7 U/mL concentration used in our isolated enzyme experiments. ADA is also present in a number of cell lines, (Cooney, D. A. et al Biochem. Pharmacol. 1987, 36, 1765) including ATH8 cells. (Masood, R. et al Mol. Pharmacol. 1990, 57, 590) Additional studies are underway to quantitate the effects of media and cellular ADA on ddN analogues, and will be reported at a future time.

In order to further establish the importance of ADA in the anti-HIV experiments, the effect of the powerful ADA inhibitor, 2'-deoxycoformycin (dCF), was evaluated. dCF affected the compounds in this study in different ways when added to the in vitro anti-HIV test system (Table II). dCF alone (5 µM), did not produce significant toxicity or protection of ATH8 cells against the effects of HIV-1. Similarly, there were no important changes in the protection afforded by ddA and its 2' fluoro analogue, 1a, in the presence of dCF. Toxicity, however, appeared to be potentiated in each instance. The ddA/dCF anti-HIV results are consistent with reported data (Cooney, D. A. et al Biochem. Pharmacol. 1987, 36, 1765). The effects observed were quite different when dCF was used in combination with the $N^6$-methyl (1f) and 6-chloro (1i) compounds. In these cases, protection was either abolished or greatly decreased relative to experiments conducted in the absence of dCF (Table II). This is qualitatively consistent with the isolated enzyme data shown in FIG. 1 and Table III.

As a consequence of the above results, studies were conducted to evaluate the effect of augmenting the HIV/ATH8 test system with additional ADA. In these experiments (Table IV), the combination of 10 µM if ($N^6$-methyl analogue) and ADA (0.7 U/mL) gave 90% protection, whereas 1f, alone, at the same concentration gave only 13% protection. Compound 1a with supplementary ADA under the same conditions did not change its activity. ADA by itself neither influenced the viability nor protected infected ATH8 cells. These data suggest that 1f and 1i are prodrug forms of 2'-F-dd-ara-I (1b), which require hydrolysis by ADA as a necessary first step in their activation.

TABLE III

Adenosine Deamimase/Dideoxynucleoside Kinetic Parameters[a]

| Substrate | $K_M$ (Molar) | vmax (µmol/min/U) | Measured Relative Rate[b] |
|---|---|---|---|
| ddA | $1.4 \times 10^{-5}$ | 1.32 | 100 |
| 2'-F-dd-ara-A (1a) | $3.3 \times 10^{-4}$ | $2.3 \times 10^{-1}$ | 6.0 |
| 6-Cl-2'-F-dd-ara-P (1i) | $7.5 \times 10^{-3}$ | $2.6 \times 10^{-2}$ | 0.06 |
| $N^6$—$CH_3$-2'-F-dd-ara-A (1f) | $1.1 \times 10^{-4}$ | $5.5 \times 10^{-4}$ | 0.04 |

TABLE III-continued

Adenosine Deamimase/Dideoxynucleoside Kinetic Parameters[a]

| Substrate | $K_M$ (Molar) | vmax (μmol/min/U) | Measured Relative Rate[b] |
|---|---|---|---|

[a]pH 7.4 and 37° C.
[b]Measured at 50 μM substrate concentration

TABLE IV

Effect of Added Adenosine Deaminase (ADA) or 2'-Deoxycoformycin (dCF) on the Anti-HIV Activity of 10 μM Compound 1f.

| Additive | % Protection[a] |
|---|---|
| None (10 μM 1f only) | 13% |
| dCF (2 μM) | <10% |
| ADA (0.7 U/ml) | 90% |

[a]Protection of ATHS cells from the cytopathogenic effects of $HIV_{IIIB}$.

TABLE V

Elemental Analyses

| Compound | Theory | Found |
|---|---|---|
| 1c | C: 50.42 | 50.57 |
| | H: 4.62 | 4.70 |
| | N: 23.53 | 23.49 |
| | F: 7.98 | 8.03 |
| 1d | C: 49.43 | 49.54 |
| | H: 5.24 | 5.24 |
| | N: 26.22 | 26.15 |
| 1e 0.8 $H_2O$ | C: 48.75 | 48.83 |
| | H: 5.96 | 5.84 |
| | N: 23.70 | 22.97 |
| 1f 0.7 $H_2O$ | C: 47.14 | 47.08 |
| | H: 5.71 | 5.42 |
| | N: 25.00 | 24.63 |
| 1g 0.2 $H_2O$ | C: 56.51 | 56.21 |
| | H: 4.43 | 4.52 |
| | N: 19.39 | 19.38 |
| | F: 5.26 | 5.47 |
| 1h | C: 49.44 | 49.56 |
| | H: 5.24 | 5.30 |
| | N: 26.22 | 26.20 |
| | F: 7.12 | 7.19 |
| 1i | C: 44.12 | 43.84 |
| | H: 3.67 | 3.65 |
| | N: 20.58 | 20.36 |
| 4a 0.2 $H_2O$ | C: 46.58 | 46.84 |
| | H: 4.43 | 4.75 |
| | N: 21.74 | 21.54 |
| | F: 7.38 | 6.96 |
| 5 0.5 $H_2O$ | C: 50.93 | 50.55 |
| | H: 6.90 | 6.73 |
| | N: 14.85 | 15.15 |
| 10 0.5 $H_2O$ | C: 50.25 | 49.93 |
| | H: 7.14 | 7.24 |
| | N: 17.24 | 17.70 |
| 21 $H_2O$ | C: 41.81 | 41.67 |
| | H: 4.88 | 4.92 |
| | N: 24.39 | 24.11 |
| | F: 6.62 | 6.73 |

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made (for example, BO— or YO— of Formulas I-VIII can be Ph—O—C—O—) without departing from the true scope of the invention and appended claims.

What is claimed is:

1. A compound of the formula:

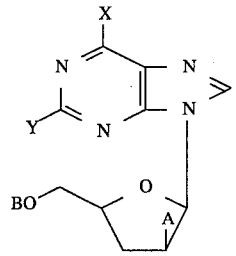

wherein

A is F;

B is H;

Y is H or $NH_2$; and

X is selected from the group consisting of halogen, NHR or OR, wherein

R is $C_{1-8}$ alkyl, straight chain or branched chain, and NROR, wherein R is H or $C_{1-8}$ alkyl, straight chain or branched chain.

2. The compound according to claim 1, wherein A is F; B is H; Y is H or $NH_2$; and X is Cl.

3. The compound according to claim 1, wherein A is F; B is H; Y is H or $NH_2$; and X is $NH(CH_3)$.

4. The compound according to claim 1, wherein A is F; B is H; Y is H or $NH_2$; and X is $O(CH_3)$.

5. The compound according to claim, 1, wherein A is F; B is H; Y is H or $NH_2$; and X is NHOH.

6. The compound according to claim 1, wherein A is F; B is H; Y is H or $NH_2$; and X is $NHOCH_3$.

7. The compound according to claim 1, wherein A is F; B is H; Y is H or $NH_2$; and X is $N(CH_3)OH$.

8. The compound according to claim 1, wherein A is F; B is H; Y is H or $NH_2$; and X is selected from the group consisting of halogen, NHR, or OR, wherein R is $C_{1-4}$ alkyl, and NROR, wherein R is H or $C_{1-4}$ alkyl.

9. The compound according to claim 8, wherein A is F; B is H; Y is H or $NH_2$; and X is Cl.

10. The compound according to claim 8, wherein A is F; B is H; Y is H or $NH_2$; and X is $NH(CH_3)$.

11. The compound according to claim 8, wherein A is F; B is H; Y is H or $NH_2$; and X is $O(CH_3)$.

12. The compound according to claim 8, wherein A is F; B is H; Y is H or $NH_2$; and X is NHOH.

13. The compound according to claim 8, wherein A is F; B is H; Y is H or $NH_2$; and X is $NHOCH_3$.

14. The compound according to claim 8, wherein A is F; B is H; Y is H or $NH_2$; and X is $N(CH_3)OH$.

15. The compound according to claim 1 or claim 8, wherein A is F; B is H; Y is H or $NH_2$; and X is $NH(C_2H_5)$.

16. The compound according to claim 1 or claim 8, wherein A is F; B is H; Y is H or $NH_2$; and X is $O(C_2H_5)$.

17. A composition comprising the compound according to claim 1, and an acceptable carrier, diluent, or excipient.

18. The composition according to claim 15, wherein in the compound of the composition, A is F; B is H; Y is H or $NH_2$ and X is Cl.

* * * * *

UNITED STATES PATENT AND TRADEMARK OFFICE
CERTIFICATE OF CORRECTION

PATENT NO.    : 5,459,256
DATED         : October 17, 1995
INVENTOR(S)   : Victor E. Marquez et al.

It is certified that error appears in the above-identified patent and that said Letters Patent is hereby corrected as shown below:

In Claim 18, Column 26, line 61, please delete "claim 15" and insert -- claim 17 --.

On the face of the issued patent, in the list of inventors, after "Victor E. Marquez, Gaithersburg;" please delete "John S. Driscoll, Rockville;".

In the list of inventors, before "Victor E. Marquez, Gaithersburg;" please insert -- John S. DRISCOLL, Rockville; --.

Signed and Sealed this

Sixth Day of August, 1996

Attest:

BRUCE LEHMAN

Attesting Officer

Commissioner of Patents and Trademarks